United States Patent
Coute' et al.

(10) Patent No.: US 6,673,978 B2
(45) Date of Patent: Jan. 6, 2004

(54) PROCESS FOR MAKING OLEFINS

(75) Inventors: Nicolas P. Coute', Houston, TX (US); Keith H. Kuechler, Friendswood, TX (US); Paul N. Chisholm, Houston, TX (US); Stephen N. Vaughn, Kingwood, TX (US); James R. Lattner, Seabrook, TX (US); William L. Kuechler, Sr., Hilton Head, SC (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 76 days.

(21) Appl. No.: 09/887,860

(22) Filed: Jun. 22, 2001

(65) Prior Publication Data

US 2003/0004384 A1 Jan. 2, 2003

Related U.S. Application Data

(60) Provisional application No. 60/290,236, filed on May 1, 2001.

(51) Int. Cl.[7] ............................................... C07C 2/207
(52) U.S. Cl. ..................................... 585/634; 585/640
(58) Field of Search ................................. 585/634, 640

(56) References Cited

U.S. PATENT DOCUMENTS

| | | | |
|---|---|---|---|
| 3,258,455 A | 6/1966 | Natta et al. | 260/93.7 |
| 3,305,538 A | 2/1967 | Natta et al. | 260/93.7 |
| 3,364,190 A | 1/1968 | Emrick | 260/93.7 |
| 3,645,992 A | 2/1972 | Elston | 260/80.78 |
| 4,076,698 A | 2/1978 | Anderson et al. | 526/348.6 |
| 4,243,691 A | 1/1981 | Mohlenkamp, Jr et al. | 426/649 |
| 4,302,565 A | 11/1981 | Goeke et al. | 526/88 |
| 4,440,871 A | 4/1984 | Lok et al. | 502/214 |
| 4,499,327 A | 2/1985 | Kaiser | 585/640 |
| 4,567,029 A | 1/1986 | Wilson et al. | 423/306 |
| 4,659,685 A | 4/1987 | Coleman, III et al. | 502/113 |
| 4,861,743 A | 8/1989 | Flank et al. | 502/214 |
| 4,873,390 A | 10/1989 | Lewis et al. | 585/638 |
| 5,096,684 A | 3/1992 | Guth et al. | 423/306 |
| 5,126,308 A | 6/1992 | Barger et al. | 502/214 |
| 5,892,079 A | 4/1999 | Wilson, Jr. | 556/11 |
| 6,023,005 A | 2/2000 | Lattner et al. | 585/639 |
| 6,166,282 A | 12/2000 | Miller | 585/638 |
| 6,437,208 B1 * | 8/2002 | Kuechler et al. | 585/640 |
| 6,455,747 B1 * | 9/2002 | Lattner et al. | 585/638 |

OTHER PUBLICATIONS

Blackwell et al., "Solid–State NMR of Silicoaluminophosphate Molecular Sieves and Aluminophosphate Materials", *J. Phys. Chem.*, vol. 92, pp. 3965–3970 (1988).

"Experimental Techniques", *Circulating Fluidized Beds*, Grace, Avidan, & Knowlton, eds., Blackie, pp. 336–337 (1997).

* cited by examiner

*Primary Examiner*—Thuan D. Dang

(57) ABSTRACT

Disclosed is a method for converting an oxygenate feedstock to an olefin product. In particular, the method incorporates the use of a silicoaluminophosphate molecular sieve catalyst in the manufacture of ethylene and propylene. The method includes contacting an oxygenate-containing feedstock with a silicoaluminophosphate molecular sieve catalyst to form the olefin-containing product in a fluidized bed reactor apparatus including at least a reaction zone and a recirculation zone. Certain ratios of the mass of catalyst in the reaction zone to that of the sum of the mass of catalyst in both the reaction zone and the recirculation zone within the reactor apparatus are specified.

94 Claims, 5 Drawing Sheets

US 6,673,978 B2

PROCESS FOR MAKING OLEFINS

This application claims priority of U.S. provisional application No. 60/290,236, filed May 11, 2001 which is hereby incorporated by reference in its entirety.

FIELD OF THE INVENTION

This invention relates to converting an oxygenate feedstock to an olefin product. In particular, this invention relates to converting an oxygenate feed to an olefin in a reaction apparatus in which catalyst is kept in a moving state throughout a reaction zone and a recirculation zone.

BACKGROUND OF THE INVENTION

Demand for polyolefins, e.g., polyethylene and polypropylene, has been steadily increasing. It is projected that the increased demand for polyolefins will outpace the availability of raw materials, e.g., ethylene and propylene, from which polyolefins can be made.

Olefins which are used to make polyolefins have been traditionally produced from petroleum feedstocks by either catalytic or steam cracking of the petroleum. The cost of petroleum cracking has steadily increased, however, making it important to find alternative feedstock sources for olefins.

Oxygenates are a promising alternative feedstock for making olefins. Particularly promising oxygenate feedstocks are alcohols, such as methanol and ethanol, dimethyl ether, methyl ethyl ether, diethyl ether, dimethyl carbonate, and methyl formate. Many of these oxygenates can be produced by fermentation, or from synthesis gas derived from natural gas, petroleum liquids, carbonaceous materials such as coal, recycled plastics, municipal wastes, or any appropriate organic material. Because of the wide variety of sources, oxygenates have promise as an economical source for olefin production.

One way in which olefins can be made from the alternative oxygenate feedstocks is by catalytic conversion, hereinafter called an "oxygenate conversion reaction." In U.S. Pat. No. 4,499,327, for example, a catalytic process for converting methanol to olefins is described. The catalyst used in that process contains a silicoaluminophosphate (SAPO) molecular sieve.

Of course it is highly desirable to convert as much of the oxygenate feedstock as possible into as much ethylene and propylene as possible. U.S. Pat. No. 4,873,390 describes a method of increasing the amount of ethylene and propylene produced from the catalytic conversion of oxygenate feedstock, preferably in a fluidized bed reaction system, by controlling the amount of carbonaceous deposits on the catalyst returned from a step of contacting the catalyst with a regeneration medium to a step recontacting the regenerated catalyst with the oxygenate feedstock. The catalyst that is used in the process also contains a SAPO molecular sieve.

U.S. Pat. No. 6,023,005 also describes a method of increasing the amount of ethylene and propylene produced from the catalytic conversion of oxygenate feedstock, preferably in a fluidized bed reaction system, by controlling the amount of carbonaceous deposits on the catalyst returned from a step of contacting the catalyst with a regeneration medium to a step recontacting the regenerated catalyst with the oxygenate feedstock. The patent further discloses mixing the regenerated catalyst with portion of catalyst flowing out of the reaction zone and contacting the catalyst mixture with the oxygenate feedstock. The catalyst that is used in the process also contains a SAPO molecular sieve.

U.S. Pat. No. 6,166,282 discloses a method of reducing the amount of total catalyst required in the catalytic conversion of oxygenate feedstock and enhancing conversion to desired products, in a fluidized bed reaction system, by employing both a dense phase and a transition phase reaction zone, operating at distinct gas superficial velocities. Further, reference again is made to returning a portion of catalyst flowing out of the reaction zone to recontact with the oxygenate feedstock. Again, the catalyst used in the process contains a SAPO molecular sieve.

In view of the importance of how catalyst is managed in the reaction systems associated with conversion of oxygenate feedstocks to olefins over SAPO molecular sieves, improved processes are sought to obtain desired conversion products while inhibiting the conversion to undesirable byproducts. More specifically, improved fluidized bed oxygenate conversion processes are sought which provide optimal catalyst inventories within a reactor apparatus to enhance the conversion to the desired products and suppress the conversion to undesirable byproducts.

SUMMARY OF THE INVENTION

The present invention solves the current needs in the art by providing a method for converting an oxygenate feedstock to a product including ethylene and propylene in a fluidized bed reactor. One embodiment of the method of the present invention comprises the following steps: providing an oxygenate feedstock, a catalyst that incorporates a SAPO molecular sieve, and a reactor apparatus including at least a reaction zone and a recirculation zone, wherein the temperature in at least one point in each of the reaction zone and the recirculation zone is at least about 250° C.; contacting the feedstock with the catalyst in the reaction zone under conditions effective to convert the feedstock to a product including prime olefins, the conditions including a GSV of at least about 0.1 m/s at at least one point in the reaction zone; having at least a portion of the catalyst in the reaction zone flow to the recirculation zone; and having a ratio of the mass of said catalyst in the reaction zone to that of the sum of the mass of the catalyst in both the reaction zone and the recirculation zone of between at least 0.01 and no greater than 0.99.

Another embodiment of the present invention is also directed to a method for converting an oxygenate feedstock to a product including ethylene and propylene in a fluidized bed reactor. The method comprises the following steps: providing an oxygenate feedstock, a catalyst that incorporates a SAPO molecular sieve, and a reactor apparatus including at least a reaction zone and a recirculation zone, wherein the temperature in at least one point in each of the reaction zone and the recirculation zone is at least about 250° C.; contacting the feedstock with the catalyst in the reaction zone under conditions effective to convert the feedstock to a product including prime olefins, the conditions including a GSV of greater than about 0.5 m/s at at least one point in said reaction zone; recirculating the catalyst to establish a temperature differential; and having a ratio of the mass of said catalyst in the reaction zone to that of the sum of the mass of the catalyst in both the reaction zone and the recirculation zone of between at least 0.01 and no greater than 0.99.

Yet another embodiment of the present invention is directed to a method for converting an oxygenate feedstock to a product including ethylene and propylene in a fluidized bed reactor. The method comprises the following steps: providing an oxygenate feedstock, a catalyst that incorporates a SAPO molecular sieve, and a reactor apparatus including at least a reaction zone and a recirculation zone, wherein the temperature in at least one point in each of the reaction zone and the recirculation zone is at least about 250° C.; contacting the feedstock with the catalyst in the reaction zone under conditions effective to convert the feedstock to a product including prime olefins, the conditions including a GSV of at least about 0.1 m/s at at least one point in said reaction zone; having an ACFE index in the reactor apparatus of at least about 1.0; and having a ratio of the mass of the catalyst in the reaction zone to that of the sum of the mass of the catalyst in both the reaction zone and the recirculation zone of between at least 0.01 and no greater than 0.99.

These and other advantages of the present invention shall become apparant from the following detailed description, the attached figures and the appended claims.

DETAILED DESCRIPTION OF THE INVENTION

Figure 1:
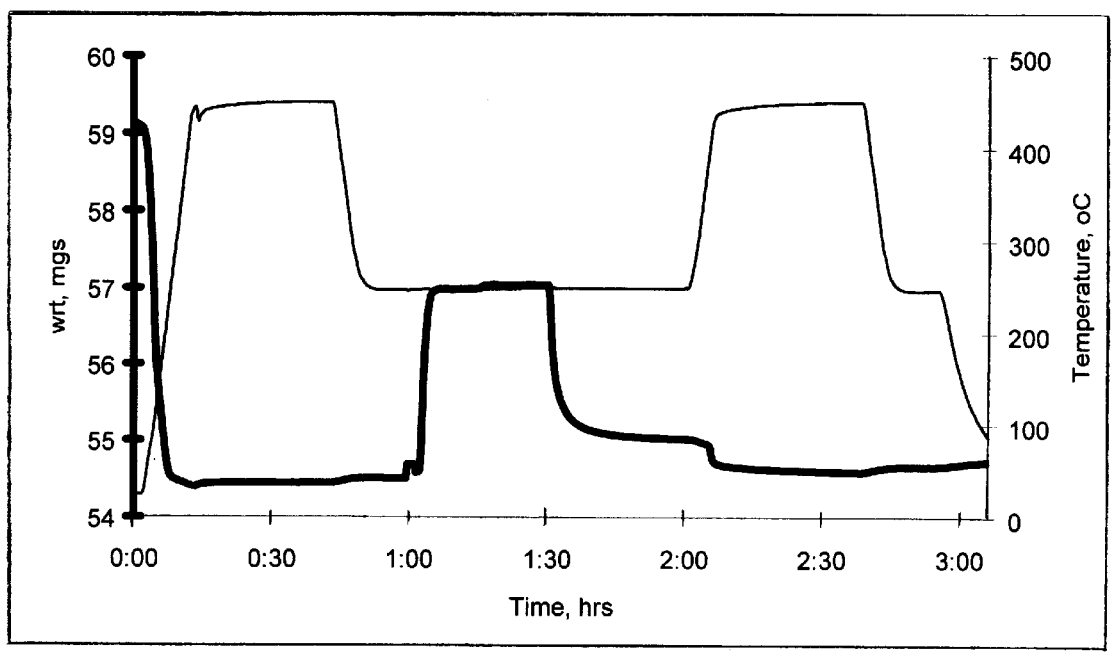
FIG. 1 is a graph of the results of a thermogravimetric analysis of an oxygenate conversion reaction at 250° C. and exposure of the molecular sieve utilized to various temperatures.

Silicoaluminophosphate (SAPO) molecular sieves serve as particularly desirable catalyst materials in converting oxygenate feedstocks to olefin compositions. They make particularly good catalysts for producing olefins such as ethylene and propylene from oxygenate compounds. As used herein, the term prime olefins refers to ethylene and propylene.

When olefinic hydrocarbon or oxygenate feedstocks are contacted with a SAPO molecular sieve at a temperature above about 250° C., those feedstocks undergo an oxygenate conversion reaction to form various products, including prime olefins. During this reaction, carbonaceous deposits, hereinafter synonymous with the term "coke," are also formed within the SAPO molecular sieve, which cause the SAPO molecular sieve weight to increase continuously with time, and cause the SAPO molecular sieve reaction performance to change with time. Further, the SAPO molecular sieve will, at points in time following exposure to feedstock, contain entrained within the microporous structure of the sieve the feedstock introduced and product made as they make their way into and out of its microporous structure. This causes an increase in SAPO molecular sieve weight immediately following exposure to feedstock, but which increase stops shortly thereafter as an equilibrium between incoming and outgoing material is quickly established.

The inventors have discovered that a SAPO molecular sieve, after having been exposed to feedstock and now containing carbonaceous deposits and entrained feedstock and product, will undergo a transformation after the exposure to feedstock is reduced or ceased, when exposed to a temperature of greater than about 250° C. This transformation manifests itself in a loss of weight of the SAPO molecular sieve through the generation of a product richer in undesirable byproducts than that obtained with exposure to feedstock. Hereinafter, this phenomena will be called "catalyst decay," and the product obtained from such a phenomena will be called "catalyst decay products."

The recognition of this previously unknown phenomena has important implications to the optimal manner in which the oxygenate conversion reaction with SAPO catalysts should be conducted in fluidized bed reactors. In fluidized bed reactors, the catalyst is allowed to flow (is "fluidized") within a reaction zone using the motive force of the feedstock and products, and possibly diluents also flowing within the reaction zone. At least a portion of the fluidized catalyst may flow out of the reaction zone into a recirculation zone, where it may become separated from the reaction product and any unconverted feedstock and diluent, collected, or routed to various locations, and require the establishment of some measure of catalyst inventory in the recirculation zone. The catalyst within the recirculation zone may be at suboptimum conditions relative to those within the reaction zone and thus subject to the undesirable byproduct generation phenomena described above. In the method of the present invention, the gas superficial velocity in the reaction zone should be sufficient to fluidize the catalyst and provide flow of at least a portion the catalyst from the reaction zone to the recirculation zone. Typically, the gas superficial velocity at at least one point in the reaction zone should be at least about 0.1 meter per second. Further, in the instant invention, the ratio of the mass of catalyst in the reaction zone to that of sum of the mass of the catalyst in both the reaction zone and the recirculation zone may be within a certain range of values. This range of values is from at least 0.01, below which highly undesirable overall selectivities are obtained due to the substantial generation of catalyst decay products, to no greater than 0.99, above which equipment designs to provide such a low inventory of catalyst in the recirculation zone become undesirably expensive, complicated or operationally problematic.

The catalyst that is used in this invention is one that incorporates a silicoaluminophosphate (SAPO) molecular sieve. The molecular sieve comprises a three-dimensional microporous crystal framework structure of $[SiO_2]$, $[AlO_2]$ and $[PO_2]$ corner sharing tetrahedral units. The way Si is incorporated into the structure can be determined by $^{29}$Si MAS NMR. See Blackwell and Pafton, *J. Phys. Chem.*, 92, 3965 (1988). The desired SAPO molecular sieves will exhibit one or more peaks in the $^{29}$Si MAS NMR, with a chemical shift δ(Si) in the range of −88 to −96 ppm and with a combined peak area in that range of at least 20% of the total peak area of all peaks with a chemical shift δ(Si) in the range of −88 ppm to −115 ppm, where the δ(Si) chemical shifts refer to external tetramethylsilane (TMS).

It is preferred that a silicoaluminophosphate molecular sieve used in this invention has a relatively low $Si/Al_2$ ratio. In general, the lower the $Si/Al_2$ ratio, the lower the $C_1$–$C_4$ saturates selectivity, particularly propane selectivity. A $Si/Al_2$ ratio of less than 0.65 is desirable, with a $Si/Al_2$ ratio of not greater than 0.40 being preferred, and a $Si/Al_2$ ratio of not greater than 0.32 being particularly preferred. A $Si/Al_2$ ratio of not greater than 0.20 is most preferred.

Silicoaluminophosphate molecular sieves are generally classified as being microporous materials having 8, 10, or 12 membered ring structures. These ring structures can have an average pore size ranging from about 3.5–15 angstroms. Preferred are the small pore SAPO molecular sieves having an average pore size of less than about 5 angstroms, preferably an average pore size ranging from about 3.5 to 5 angstroms, more preferably from 3.5 to 4.2 angstroms. These pore sizes are typical of molecular sieves having 8 membered rings.

In general, silicoaluminophosphate molecular sieves comprise a molecular framework of corner-sharing [SiO2], [AlO$_2$], and [PO$_2$] tetrahedral units. This type of framework is effective in converting various oxygenates into olefin products.

The [PO$_2$] tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The [AlO$_2$] tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The [SiO$_2$] tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanide elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a [MeO$_2$] tetrahedral unit. The [MeO$_2$] tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

An aluminophosphate (ALPO) molecular sieve can also be included in the catalyst composition. Aluminophosphate molecular sieves are crystalline microporous oxides which can have an AlPO$_4$ framework. They can have additional elements within the framework, typically have uniform pore dimensions ranging from about 3 angstroms to about 10 angstroms, and are capable of making size selective separations of molecular species. More than two dozen structure types have been reported, including zeolite topological analogues. A more detailed description of the background and synthesis of aluminophosphates are found in U.S. Pat. No. 4,310,440, which is incorporated herein by reference in its entirety. Preferred ALPO structures are ALPO-5, ALPO-11, ALPO-18, ALPO-31, ALPO-34, ALPO-36, ALPO-37, and ALPO-46.

The ALPOs can also include a metal substituent in its framework. Preferably, the metal is selected from the group consisting of magnesium, manganese, zinc, cobalt, and mixtures thereof. These materials preferably exhibit adsorption, ion-exchange and/or catalytic properties similar to aluminosilicate, aluminophosphate and silica aluminophosphate molecular sieve compositions. Members of this class and their preparation are described in U.S. Pat. No. 4,567,029, incorporated herein by reference in its entirety.

The metal containing ALPOs have a three-dimensional microporous crystal framework structure of MO$_2$, AlO$_2$ and PO$_2$ tetrahedral units. These as manufactured structures (which contain template prior to calcination) can be represented by empirical chemical composition, on an anhydrous basis, as:

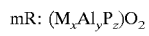

mR: (M$_x$Al$_y$P$_z$)O$_2$ wherein "R" represents at least one organic templating agent present in the intracrystalline pore system; "m" represents the moles of "R" present per mole of (M$_x$Al$_y$P$_z$)O$_2$ and has a value of from zero to 0.3, the maximum value in each case depending upon the molecular dimensions of the templating agent and the available void volume of the pore system of the particular metal aluminophosphate involved, "x", "y", and "z" represent the mole fractions of the metal "M", (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

The silicoaluminophosphate molecular sieves are synthesized by hydrothermal crystallization methods generally known in the art. See, for example, U.S. Pat. Nos. 4,440,871; 4,861,743; 5,096,684; and 5,126,308, the methods of making of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100–250° C., until a crystalline product is formed. Formation of the crystalline product can take anywhere from around 2 hours to as much as 2 weeks. In some cases, stirring or seeding with crystalline material will facilitate the formation of the product.

Typically, the molecular sieve product will be formed in solution. It can be recovered by standard means, such as by centrifugation or filtration. The product can also be washed, recovered by the same means, and dried.

As a result of the crystallization process, the recovered sieve contains within its pores at least a portion of the template used in making the initial reaction mixture. The crystalline structure essentially wraps around the template, and the template must be removed so that the molecular sieve can exhibit catalytic activity. Once the template is removed, the crystalline structure that remains has what is typically called an intracrystalline pore system.

In many cases, depending upon the nature of the final product formed, the template may be too large to be eluted from the intracrystalline pore system. In such a case, the template can be removed by a heat treatment process. For example, the template can be calcined, or essentially combusted, in the presence of an oxygen-containing gas, by contacting the template-containing sieve in the presence of the oxygen-containing gas and heating at temperatures from 200° C. to 900° C. In some cases, it may be desirable to heat in an environment having a low oxygen concentration. In these cases, however, the result will typically be a breakdown of the template into a smaller component, rather than by the combustion process. This type of process can be used for partial or complete removal of the template from the intracrystalline pore system. In other cases, with smaller templates, complete or partial removal from the sieve can be accomplished by conventional desorption processes such as those used in making standard zeolites.

The reaction mixture can contain one or more templates. Templates are structure directing or affecting agents, and typically contain nitrogen, phosphorus, oxygen, carbon, hydrogen or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly directing than another.

Representative templates include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof. Preferred templates are triethylamine, cyclohexylamine, piperidine, pyridine, isopropylamine, tetraethyl ammonium salts, dipropylamine, and mixtures thereof. The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Preferred tetraethyl ammonium salts are tetraethyl ammonium hydroxide and tetraethyl ammonium phosphate.

The SAPO molecular sieve structure can be effectively controlled using combinations of templates. For example, in a particularly preferred embodiment, the SAPO molecular sieve is manufactured using a template combination of TEAOH and dipropylamine. This combination results in a particularly desirable SAPO structure for the conversion of oxygenates, particularly methanol and dimethyl ether, to light olefins such as ethylene and propylene.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof. These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 to about 1 cal/g-° C., more preferably from about 0.1 to about 0.8 cal/g-° C., most preferably from about 0.1 to about 0.5 cal/g-° C.

Additional molecular sieve materials can be included as a part of the SAPO catalyst composition or they can be used as separate molecular sieve catalysts in admixture with the SAPO catalyst if desired. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof. These small and medium pore molecular sieves are described in greater detail in the *Atlas of Zeolite Structural Types*, W. M. Meier and D. H. Olsen, Butterworth Heineman, 3rd ed., 1997, the detailed description of which is explicitly incorporated herein by reference. Preferred molecular sieves which can be combined with a silicoaluminophosphate catalyst include ZSM-5, ZSM-34, erionite, and chabazite.

The catalyst composition preferably comprises about 1% to about 99%, more preferably about 5% to about 90%, and most preferably about 10% to about 80%, by weight of molecular sieve. It is also preferred that the catalyst composition have a particle size of from about 20 $\mu$ to 3,000 $\mu$, more preferably about 30 $\mu$ to 200 $\mu$, most preferably about 50$\mu$ to 150 $\mu$.

The catalyst can be subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof.

The oxygenate feedstock of this invention comprises at least one organic compound which contains at least one oxygen atom, such as aliphatic alcohols, ethers, or carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

The method of making the preferred olefin product in this invention can include the additional step of making these compositions from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidization.

One or more inert diluents may be present in the feedstock, for example, in an amount of from 1 to 99 molar percent, based on the total number of moles of all feed and diluent components fed to the reaction zone (or catalyst). As defined herein, diluents are compositions which are essentially non-reactive across a molecular sieve catalyst, and primarily function to make the oxygenates in the feedstock less concentrated. Typical diluents include, but are not necessarily limited to helium, argon, nitrogen, carbon monoxide, carbon dioxide, water, essentially non-reactive paraffins (especially the alkanes such as methane, ethane, and propane), essentially non-reactive alkylenes, essentially non-reactive aromatic compounds, and mixtures thereof. The preferred diluents are water and nitrogen. Water can be injected in either liquid or vapor form.

Hydrocarbons can also be included as part of the feedstock, i.e., as co-feed. As defined herein, hydrocarbons included with the feedstock are hydrocarbon compositions which are converted to another chemical arrangement when contacted with molecular sieve catalyst. These hydrocarbons can include olefins, reactive paraffins, reactive alkylaromatics, reactive aromatics or mixtures thereof. Preferred hydrocarbon co-feeds include, propylene, butylene, pentylene, $C_4^+$ hydrocarbon mixtures, $C_5^+$ hydrocarbon mixtures, and mixtures thereof. More preferred as co-feeds are a $C_4^+$ hydrocarbon mixtures, with the most preferred being $C_4^+$ hydrocarbon mixtures which are obtained from separation and recycle of oxygenate conversion product.

The method of the present invention is conducted in a reactor apparatus. As used herein, the term "reactor apparatus" refers to an apparatus that includes at least a reaction zone and a recirculation zone. As further used herein, the term "reaction zone" is used synonymously with the term "reactor," and refers to the portion or portions of a reactor apparatus in which the oxygenate feedstock is contacted with the catalyst at conditions effective to convert the oxygenate portion of the feedstock into a product comprising prime olefins, and which comprises an inlet zone. An "inlet zone" is the portion or portions of the reaction zone into which oxygenate feedstock is introduced to the reaction zone to first come into contact with catalyst. The reaction zone may be in fluid communication with the recirculation zone. As used herein, the term "recirculation zone" refers to the portion or portions of a reactor apparatus other than the reaction zone where catalyst is found, typically comprising a disengaging zone and a catalyst distribution zone. The "disengaging zone" is the portion or portions of the recirculation zone which serve to separate the catalyst and any additional solids from the oxygenate conversion reaction product and any unreacted oxygenate feedstock and diluent. The disengaging zone may be in fluid communication with a catalyst distribution zone. The "catalyst distribution zone" is a portion of the recirculation zone in which catalyst is transported from one part of a reaction zone to another, one part of a recirculation zone to another, or to another item of equipment outside the reactor apparatus, for example, a catalyst regenerator as described below. Optionally, catalyst from the recirculation zone or from outside the reactor apparatus may be directed to an inlet zone. Desirably, the reaction zone is positioned between an inlet zone and a disengaging zone.

In a typical fluidized bed apparatus of the present invention, the reaction zone may have various three dimensional geometries, including, for example, open circular, triangular, square and other polyhedral ducts of various lengths. Those ducts may have varying cross sectional shapes or areas at various places along their length. Further, those reaction zone ducts may be only partially open, containing within them auxiliary elements, including, for example, other pipes or ducts carrying heat transfer fluid. In other embodiments, the reaction zone may be comprised of more than one portion of the reactor apparatus, i.e., there may be more than one portion of the reactor apparatus into which oxygenate feedstock is introduced and where an oxygenate conversion reaction takes place at various conditions. For example, there may be a first, main portion of the reaction zone with a large cross sectional area and volume, and other portions with smaller cross sectional areas and volumes. This may be the case when using oxygenate feedstock as the lift gas for transferring regenerated catalyst from the regenerator to the reactor apparatus, or if oxygenate feedstock were to be introduced to an auxiliary element such as a catalyst cooler, as may be seen when examining the examples and drawings which follow.

In a typical reactor apparatus of the present invention, elements of the recirculation zone may include a termination vessel volume, cyclone separators, the diplegs transferring catalyst from the cyclone separators, conduits to and from auxiliary devices such as catalyst strippers, catalyst coolers and heat exchangers, and those auxiliary devices themselves, conduits to equipment other than the reactor apparatus (e.g., a catalyst regenerator), and control devices within those conduits (e.g., slide valves), among others well known to those skilled in the art. In each of these types of elements in a recirculation zone, the catalyst is at suboptimal conditions relative to those within the reaction zone. Certain elements may have characteristics of both a disengaging zone and a catalyst distribution zone, for example, a conduit in fluid communication with the reaction zone leading to a catalyst cooler.

Typically, conduits coming from a regenerator to the reactor apparatus, and a regenerator itself, which contain catalyst that has deliberately had most organic content removed or modified through exposure to a regeneration medium at high temperatures and have not yet been re-exposed to oxygenate feedstock, are not considered a part of the recirculation zone, and the catalyst contained therein is not used in the calculation of the masses of catalyst in the zones of the reactor apparatus. (As discussed below, a conduit coming from a regenerator may have introduced to it oxygenate feedstock as a lift gas, under which circumstances such conduit is then a portion of the reaction zone).

Typically, all products generated in the reactor apparatus, whether oxygenate conversion products from the reaction zone or catalyst decay products from the recirculation zone, are combined within the reactor apparatus and exit the reactor apparatus as a mixture. In some embodiments, products may be captured separately from various elements of the apparatus. For example, the materials generated by an element such as the catalyst stripper may be captured apart from other elements such as the cyclone separators and directed to a different place in subsequent processing. Regardless, the total products generated by all elements of the reactor apparatus comprise a utilization of the feedstock, and it is those total materials whose concentration of desired products is enhanced by the method of this invention.

In the method of the present invention, the temperature in at least one point in each of the reaction zone and the recirculation zone of the reactor apparatus may vary over a wide range above about 250° C. depending, at least in part, on the catalyst, the fraction of regenerated catalyst in a catalyst mixture, the configuration of the reactor apparatus and the elements comprising the reactor apparatus, and the desired or acceptable oxygenate feedstock conversion levels and proportions of prime olefin and undesirable byproducts. Lower temperatures generally result in undesirably low rates of the oxygenate conversion reaction, and the formation rate of the desired prime olefin products in the reaction zone becomes markedly slower. Additionally, below about 250° C. the rate of catalyst decay becomes markedly slower and the generation of catalyst decay products becomes of lower concern. In one embodiment of the present invention, the temperature in at least one point in each of the reaction zone and the recirculation zone is at least about 250° C. In various other embodiments, the temperature in at least one point in each of the reaction zone and the recirculation zone is at least about 300° C., or at least about 350° C., or least about 400° C., or at least about 450° C. However, at high temperatures, the process may not form an optimum amount of prime olefin products, and the rate at which carbonaceous deposits and undesirable byproducts, particularly light saturates, form by both oxygenate conversion reaction and catalyst decay may become unattractively high. In one embodiment of the present invention, the temperature in at least one point in each of the reaction zone and the recirculation zone is no greater than about 750° C. In other embodiments, the temperature in at least one point in each of the reaction zone and the recirculation zone is no greater than about 700° C., or no greater than about 650° C., or no greater than about 600° C., or no greater than about 550° C. In alternative embodiments of the present invention, the temperature in at least one point in each of the reaction zone and the recirculation zone may be the full range, or any of the subranges contained in this paragraph, for example, between at least about 350° C. and no greater than about 650° C.

In another embodiment of the present invention, the temperature at all points in each of the reaction zone and the recirculation zone is at least about 250° C. In various other embodiments, the temperature at all points in each of the reaction zone and the recirculation zone is at least about 300° C., or at least about 350° C., or least about 400° C., or at least about 450° C. In yet another embodiment of the present invention, the temperature in at least one point in each of the reaction zone and the recirculation zone is no greater than about 750° C. In still other embodiments, the temperature at all points in each of the reaction zone and the recirculation zone is no greater than about 700° C., or no greater than about 650° C., or no greater than about 600° C., or no greater than about 550° C. In yet other alternative embodiments of the present invention, the temperature at all points in each of the reaction zone and the recirculation zone may be the full range, or any of the subranges contained in this paragraph, for example, between at least about 350° C. and no greater than about 650° C.

Prime olefins will form, although not necessarily in optimum amounts, at a wide range of pressures including, but not limited to, autogeneous pressures and pressures from about 0.1 kPa to about 5 MPa. A desired pressure is from about 5 kPa to about 1 MPa and most desirably from about 20 kPa to about 500 kPa. The foregoing pressures do not include that of a diluent, if any, and refer to the partial pressure of the feed as it relates to oxygenate feedstock and/or mixtures thereof. Pressures outside of the stated ranges may be used and are not excluded from the scope of the invention. Lower and upper extremes of pressure may adversely affect selectivity, conversion, coking rate, and/or reaction rate; however, prime olefins will still form and, for that reason, these extremes of pressure within a reactor apparatus are considered part of the present invention.

A wide range of weight hourly space velocity (WHSV) for the oxygenate conversion reaction within the reaction zone, defined as weight of total oxygenate feedstock to the reaction zone per hour per weight of molecular sieve in the catalyst in the reaction zone, function with the present invention. The total oxygenate feedstock to the reaction zone includes all oxygenate and any hydrocarbon co-feed in both the vapor and liquid phase. Diluents are not included in a determination of the WHSV. Although the catalyst may contain other materials which act as inerts, fillers or binders, the WHSV is calculated using only the weight of molecular sieve in the catalyst in the reaction zone. The WHSV is desirably high enough to maintain the catalyst in a fluidized state under the reaction conditions and within the reactor configuration and design.

Generally, the WHSV is from about 1 $hr^{-1}$ to about 5000 $hr^{-1}$, desirably from about 2 $hr^{-1}$ to about 3000 $hr^{-1}$, more desirably from about 5 $hr^{-1}$ to about 1500 $hr^{-1}$, and even more desirably from about 10 $hr^{-1}$ to about 1000 $hr^{-1}$. The applicants have discovered that operation of the oxygenate to olefin conversion reaction at a WHSV greater than 20 $hr^{-1}$ reduces the methane content in the product slate of the conversion reaction. Thus, the conversion reaction is desirably operated at a WHSV of at least about 20 $hr^{-1}$. For a feed comprising methanol, dimethyl ether, or mixtures thereof, the WHSV is desirably at least about 20 $hr^{-1}$ and more desirably from about 20 $hr^{-1}$ to about 300 $hr^{-1}$.

It is particularly preferred that the reaction conditions for making olefins from an oxygenate feedstock in the reaction zone comprise a WHSV of at least about 20 $hr^{-1}$ and a Temperature Corrected Normalized Methane Selectivity (TCNMS) of less than about 0.016. As used herein, TCNMS is defined as the Normalized Methane Selectivity (NMS) when the temperature is less than 400° C. The NMS is defined as the methane product yield divided by the ethylene product yield wherein each yield is measured on or is converted to a weight % basis. When the temperature is 400° C. or greater, the TCNMS is defined by the following equation, in which T is the average temperature within the reactor in ° C.

$$TCNMS = \frac{NMS}{1 + (((T - 400)/400) \times 14.84)}.$$

In the present invention, oxygenate conversion, referring to the oxygenate species per se and not including any hydrocarbon co-feed, should be maintained sufficiently high to avoid the need for commercially unacceptable levels of oxygenate feedstock recycling. While 100% oxygenate conversion is desired for the purpose of potentially completely avoiding oxygenate feedstock recycle, a reduction in undesirable byproducts is observed frequently when the conversion is about 99% or less, and incremental economic improvements may occur when the conversion is about 98% or less, further to about 96% or less, and still further to about 94% or less. Since recycling up to as much as about 50% of the feed can be commercially acceptable, conversion rates from about 50% to about 98% are desired. Oxygenate conversion rates may be maintained in the range of about 50% to about 99% using a number of methods familiar to persons of ordinary skill in the art. Examples include, but are not necessarily limited to, adjusting one or more of the following: reaction temperature; pressure; flow rate (weight hourly space velocity and/or gas superficial velocity); catalyst recirculation rate; reactor apparatus configuration; reactor configuration; feed composition; amount of liquid feed relative to vapor feed; amount of recirculated catalyst; degree of catalyst regeneration; and other parameters which affect the conversion.

For the purposes of the present invention, oxygenate conversion may be measured based on the total measures of oxygenate feedstock to and total effluent of prime olefins, undesirable byproducts and oxygenate feedstock from the reactor apparatus, regardless of to which particular zone or zones such oxygenate feedstock may be introduced or from which such effluent may emanate.

In the present invention, undesirable byproducts comprise anything that is not prime olefins. Some byproducts are more undesirable than others are. Examples of particularly undesirable byproducts include hydrogen and light saturates, such as methane, ethane, propane, normal butane and isobutane, and carbon monoxide and carbon dioxide. These particularly undesirable byproducts must be separated from prime olefin and other olefin products using expensive and energy intensive techniques such as cryogenic fractionation or permeable membranes, and generally, the higher their concentration the more costly is the production of desirable prime olefin and other olefin products. Another particularly undesirable byproduct is coke, which eventually must be removed from the catalyst in a catalyst regenerator, described below. Other less undesirable byproducts include $C_4$ and higher carbon number olefins and paraffins. These byproducts are undesirable because they generally have a substantially lower value in the marketplace than prime olefins. However, they are less undesirable than the other materials mentioned because they are generally more valuable than those materials, and generally easier and less costly to separate from the prime olefin products.

The catalyst decay products which the present invention seeks to suppress are comprised of a higher content of undesirable byproducts than the oxygenate conversion products emanating from the reaction zone. In one aspect of the present invention, the concentration of any one, or all, of the undesirable byproducts in the catalyst decay products may be about 1.1 to as much as about 10 times that found in the products from the reaction zone.

One important process condition of the method of the present invention is the gas superficial velocity in the reaction zone. As used herein and in the claims, the term, "gas superficial velocity," or GSV, is defined as the combined volumetric flow rate of vaporized feedstock, including diluent which can be present in the feedstock, and conversion products, divided by the cross-sectional area of the reaction zone. The oxygenate is converted to a product including a light olefin while flowing through the reaction zone, and the GSV may vary at different locations within the reaction zone depending on the total number of moles of gas present and the cross sectional area, temperature, pressure and other relevant reaction parameters at a particular location in the reaction zone.

In the method of the present invention, the gas superficial velocity in the reaction zone should be sufficient to fluidize the catalyst and provide flow of at least a portion the catalyst from the reaction zone to the recirculation zone. Typically, the gas superficial velocity at at least one point in the reaction zone should be at least about 0.1 meter per second (m/s).

In the method of the present invention, the GSV may be increased above about 0.1 meter per second to more closely approach a hydrodynamic flow regime in the reaction zone that more closely approximates plug flow. As the GSV increases above about 0.1 meter per second, a reduction in axial diffusion, or backmixing, of the gases flowing through the reactor results from a reduction in internal recirculation of solids, which carry gas with them. (Ideal plug flow behaviour occurs when elements of the homogeneous fluid reactant and product move through a reactor as plugs moving parallel to the reactor axis). Minimizing the backmixing of the gases in the reactor increases the selectivity to the desired light olefins in the oxygenate conversion reaction.

In another embodiment of the present invention, the gas superficial velocity is at least about 0.5 m/s at at least one point in the reaction zone. Desirably, the gas superficial velocity is at least about 1.0 m/s at at least one point in the reaction zone. Yet more desirably, the gas superficial velocity is at least about 2.0 m/s at at least one point in the reaction zone. Even more desirably, the gas superficial velocity is at least about 2.5 m/s at at least one point in the reaction zone. Most desirably, the GSV is at least about 4.0 m/s at at least one point in the reaction zone. In another embodiment of the present invention, the gas superficial velocity in the reaction zone is at least 0.1 m/s at all points in the reaction zone. Preferably, the gas superficial velocity is at least about 0.5 m/s at all points in the reaction zone. More preferably, the gas superficial velocity is at least about 1.0 m/s at all points in the reaction zone. Yet more preferably, the gas superficial velocity is at least about 2.0 m/s at all points in the reaction zone. Even more preferably, the gas superficial velocity is at least about 2.5 m/s at all points in the reaction zone. Most preferably, the GSV is at least about 4.0 m/s at all points in the reaction zone.

In the method of the present invention, the temperature and pressure within the reaction zone, the recirculation zone and the various elements of each may differ substantially. In one aspect, the lowest temperature within the reactor apparatus may be within about 300° C., in another aspect may be within about 150° C., and in yet another aspect within about 100° C. of the highest temperature in the reactor apparatus. In another embodiment of the present invention, the lowest pressure within the reactor apparatus may be within about 700 kPa, and in another embodiment within about 500 kPa of the highest pressure within the reactor apparatus. Typically, the pressures of catalyst and products usually vary only by about the static head required to cause each to flow to the the desired places within and out of the reactor apparatus. The temperatures usually only vary as a result of the exothermic heat of the oxygenate conversion reaction and the impact of the heat capacity of the catalyst within and returned from outside the reactor apparatus, for example, from the regenerator. Also within the scope of the present invention, embodiments may include means or configurations to change the conditions within the reactor apparatus substantially. This may include use of a catalyst cooler, or providing for return of very hot catalyst from a catalyst regenerator to a part of the reactor apparatus containing only a small amount of catalyst, or use of a jet eductor designed to substantially increase the pressure of a catalyst stream or other materials being moved around in the reaction zone or recirculation zone.

In another embodiment of the present invention, the GSV is greater than about 0.5 m/s at at least one point in the reaction zone, or alternatively greater than about 1.0 m/s, or in another alternative greater than about 2.0 m/s, or in yet another alternative greater than about 2.5 m/s, or in one other alternative greater than about 4.0 m/s, and a mass of catalyst is recirculated to control the temperature differential in the reactor by absorbing a portion of the heat generated by the conversion reaction. The temperature differential is controlled by controlling the rate at which catalyst is recirculated. The terms "recirculating the catalyst" and "catalyst recirculation," used in the context of establishing or controlling a temperature differential, both mean that at least a portion of the catalyst in the reactor is entrained with the gas going to the outlet of the reactor, separated from the gas and routed within the recirculation zone back to the inlet zone.

For this embodiment of the present invention, "temperature differential" is defined as a measurable change in temperature from the inlet zone to the outlet of the reactor. The "outlet" is the portion of the reactor at which the reactants (feed, catalyst and products) pass out of the reaction zone into the first element of the disengaging zone that eventually leads to products leaving the reactor apparatus altogether. Typically, that first element of the disengaging zone that eventually leads to products leaving the reactor apparatus altogether is a termination vessel or a cyclone separator. (This will be a first, "primary" cyclone separator if there are at least two cyclones in series, or one of the primary cyclones if there are parallel sets of cyclones in series). The temperature of the inlet zone is calculated by balancing the heat content of the total catalyst plus non-reactive solids and the total vapor fed to the inlet zone. Any sensible heat effects of the liquid feed itself are ignored in the calculation of the temperature of the inlet zone or of any other part of the reactor, and only the heat of vaporization is considered once it enters the reactor, in addition to the sensible heat impacts from the vapors produced from the liquid feed. The assumption is made that a negligible conversion of oxygenate occurs and, hence, negligible heat of reaction at the inlet zone is generated, and conversion and heat of reaction only occur to any significant extent in the reactor when the oxygenate has become a vapor.

The temperature differential established may be within a wide range of temperatures by controlling the rate of catalyst recirculation. In one aspect, the temperature differential is desirably no greater than about 150° C. In another aspect, the temperature differential is no greater than about 100° C. In yet another aspect, the temperature differential is no greater than about 50° C., and in still another aspect the temperature differential is no greater than about 20° C. It is desirable to maintain a low temperature differential in order to create conditions which are as close to isothermal as practical in the reaction zone, and thus be able to more precisely set the temperature at which the oxygenate conversion reaction may be conducted. In an optional aspect, a temperature differential is maintained by establishing the rate of catalyst recirculation in a reactor apparatus that excludes a catalyst cooler and other indirect heat transfer devices as an element of the reactor apparatus.

The rate of catalyst, comprising molecular sieve and any other materials such as binders, fillers, etc., recirculated to recontact the feed may vary over a wide range in the method of the present invention. Desirably, this rate of recirculation is from about 1 to about 100 times, more desirably from about 10 to about 80 times, and most desirably from about 10 to about 50 times the total feed rate of oxygenates to the reactor.

Desirably, the catalyst, comprising molecular sieve and any other materials such as binders, fillers, etc. should have a heat capacity of from about 0.1 to about 1 cal/g-° C., more preferably from about 0.1 to about 0.8 cal/g-° C., and most preferably from about 0.2 to about 0.5 cal/g-° C.

As additional methods for controlling the heat generated by the conversion reaction and, subsequently, the temperature differential, the present invention may include one or more or all of the following steps: providing a portion of the oxygenate portion of the feed to the reactor in a liquid form; providing at least a portion of the diluent to the reactor in a liquid form; and providing non-reactive solids to the reactor apparatus.

When a portion of the feed is provided in a liquid form, the liquid portion of the feed may be either oxygenate, diluent or a mixture of both. The liquid portion of the feed may be directly injected into the reactor, or entrained or otherwise carried into the reactor with the vapor portion of the feed or a suitable carrier gas/diluent. By providing a portion of the feed (oxygenate and/or diluent) in the liquid phase, the temperature differential can be further controlled. The exothermic heat of reaction of oxygenate conversion is partially absorbed by the endothermic heat of vaporization of the liquid portion of the feed. Controlling the proportion of liquid feed to vapor feed fed to the reactor thus allows control of the temperature differential. Introduction of liquid feed to the reactor acts in concert with the recirculation of catalyst and non-reactive solids, providing another independent variable to improve overall control of the temperature differential.

The amount of feed provided to the reactor in a liquid form, whether fed separately or jointly with the vapor feed, is from about 0.1 wt. % to about 85 wt. % of the total oxygenate content plus diluent in the feed. More desirably, the range is from about 1 wt. % to about 75 wt. % of the total oxygenate plus diluent feed, and most desirably the range is from about 5 wt. % to about 65 wt. %. The liquid and vapor portions of the feed may be the same composition, or may contain varying proportions of the same or different oxygenates and same or different diluents. One particularly effective liquid diluent is water, due to its relatively high heat of vaporization, which allows for a high impact on the reactor temperature differential with a relatively small rate. Other useful diluents are described above. Proper selection of the temperature and pressure of any appropriate oxygenate and/or diluent being fed to the reactor will ensure at least a portion is in the liquid phase as it enters the reactor and/or comes into contact with the catalyst or a vapor portion of the feed and/or diluent.

Optionally, the liquid fraction of the feed may be split into portions and introduced to the reactor at a multiplicity of locations along its length. This may be done with either the oxygenate feed, the diluent or both. Typically, this is done with the diluent portion of the feed. Another option is to provide a nozzle which introduces the total liquid fraction of the feed to the inlet zone or reactor in a manner such that the nozzle forms liquid droplets of an appropriate size distribution which, when entrained with the gas and solids introduced to the inlet zone or reactor, vaporize gradually along the length of the reactor. Either of these arrangements or a combination thereof may be used to better control the temperature differential. The means of introducing a multiplicity of liquid feed points in a reactor or designing a liquid feed nozzle to control droplet size distribution is well known in the art and is not discussed here.

Non-reactive solids which contain no molecular sieve may be mixed with the catalyst solids, and used in the reactor, and recirculated to the reactor and regenerator. These non-reactive solids have the same capability as the catalyst to provide inertial mass to control the heat generated by the conversion reaction, but are substantially inert for the purposes of oxygenate conversion. Suitable materials for use as non-reactive solids are metals, metal oxides, and mixtures thereof. Particularly suitable materials are those used as matrices for the catalyst formulation, e.g., fillers and binders such as silicas and aluminas, among others, and mixtures thereof. Desirably, the non-reactive solids should have a heat capacity of from about 0.05 to about 1 cal/g-° C., more preferably from about 0.1 to about 0.8 cal/g-° C., and most preferably from about 0.1 to about 0.5 cal/g-° C. Further, desirably, the mass proportion of non-reactive solids to catalyst is from about 0.01 to about 10, more desirably from about 0.05 to about 5.

Desirably, the rate of catalyst, comprising molecular sieve and any other materials such as binders, fillers, etc., plus non-reactive solids, recirculated to recontact the feed is from about 1 to about 200 times, more desirably from about 10 to about 160 times, and most desirably from about 10 to about 100 times the total feed rate of oxygenates to the reactor.

One skilled in the art will appreciate that the non-reactive solids may also be regenerated with the catalyst in the manner described below.

The catalyst within the recirculation zone may be present at suboptimum reaction conditions, that is, conditions different from those found in the reaction zone where the majority of conversion of oxygenates is intended to take place. This is because the catalyst may be largely unexposed to oxygenate feedstock other than what may be entrained within the microporous structure of the sieve or the mesoporous structure of the fillers and binders that comprise the catalyst, or small amounts that may be entrained outside the catalyst through macroscopic physical phenomena and the imperfect means of separation from the oxygenate conversion products and any unconverted feedstock. Further, at the point it enters the recirculation zone, the oxygenate feedstock may have been largely consumed, and thus the entrained materials, regardless of their source, will be comprised predominantly of oxygenate conversion products including prime olefins. Additionally, the catalyst may be in a dense state (relative to the reaction zone) as it flows within the recirculation zone, potentially having been largely separated from the bulk gases comprised of oxygenate and oxygenate conversion products including prime olefins. Thus, while being exposed to some temperature of at least about 250° C., the large volume catalyst and small volume of entrained materials interact at what is in essence a low space velocity, well below that considered optimum as found in the reaction zone. The catalyst in this condition tends to convert any oxygenate or prime olefins that may be present to undesirable byproducts. Additionally, other factors within the recirculation zone may lead to the catalyst being present at suboptimum condition, for example: being at a higher temperature than used in the reaction zone due to exposure to very hot catalyst returned from a regenerator, or being at a lower temperature than used in the reaction zone due to being within a catalyst cooler.

Thus, it is important in the method of the present invention to have a ratio of the mass of catalyst in the reaction zone to that of the sum of the mass of the catalyst in both the reaction zone and the recirculation zone of at least 0.01, to enhance the conversion of oxygenates to the desired products and suppress conversion to undesirable byproducts, but no greater than 0.99, above which equipment designs to provide such a low inventory of catalyst in the recirculation zone become undesirably expensive, complicated or operationally problematic. In other aspects, the ratio of the mass of catalyst in the reaction zone to that of sum of the mass of the catalyst in both the reaction zone and the recirculation zone is at least 0.01, or at least about 0.02, or at least about 0.05, or at least about 0.10, or least about 0.20, or at least about 0.30, or at least about 0.40, or at least about 0.50, and; no greater than 0.99, or no greater than about 0.98, or no greater than about 0.95, or no greater than about 0.90, or no greater than about 0.85, or no greater than about 0.80, or no greater than about 0.70, or no greater than about 0.60, and; every possible subrange subsumed therein.

Many means of measuring and calculating the mass of catalyst in a zone of a reactor apparatus of the present invention are well known to those skilled in the art. One simple means comprises a determination of the pressure differential between two different heights in the same element of a given zone in the same direction as gravity while the apparatus is operational in the method of the present invention. The pressure differential is then divided by the difference in the height, which provides an average density within the element. This average density is then multiplied by the volume of the element under consideration, which is known through straightforward geometric calculations based on the design or actual measurements of the element or elements within the zone, which provides a determination of mass in the element. Due to the large difference in the density between the oxygenate feedstock, diluents, and oxygenate conversion products within a zone under consideration and the density of the catalyst within that element, it is permissible to consider that determined mass to be the mass of catalyst within that element. The masses of each element within a zone may be added to determine the total mass within the zone. In the method of the present invention, the catalyst is moved around among the various elements in a random fashion such that an appropriate sample volume of catalyst in any zone or element therein will be very similar, in terms of the proportion of molecular sieve and binders and fillers. Thus there is typically no need to consider the actual proportion of sieve and binders and fillers in the catalyst in making the determination of the mass of the catalyst in the reaction zone and in the recirculation zone, even if different proportions are added to the reactor apparatus at different times while employing the method of this invention.

In the present invention, in the event that means to determine the mass of catalyst in certain elements during operation of the reactor apparatus are not available, for example, through the omission of appropriate pressure taps in a cyclone or cyclone diplegs in the design and construction of the reactor apparatus, one should utilize the expected mass of catalyst determined at operating design conditions as specified for the construction or utilization of the reactor apparatus or element in oxygenate conversion service. If no such design or construction specifications or calculations are available, then one should assume for the recirculation zone that the entire volume of an element, as determined from as-built geometric measurements, is full of catalyst at its normal, uncalcined bulk density prior to being introduced to the reactor apparatus, and for the reaction zone that 15% of the volume of an element, as determined from as-built geometric measurements, contains catalyst at its normal, uncalcined bulk density prior to being introduced to the reactor apparatus.

Methods of establishing and manipulating the ratio of the mass of catalyst in the reaction zone to that of the sum of the mass of the catalyst in both the reaction zone and the recirculation zone using a number of methods well known to those skilled in the art. Example include, but are not limited to, proper selection of one or more of the following: geometry of the various elements of the reactor apparatus, including the reactor vessel, cyclones, diplegs, conduits and transfer lines, and auxiliary equipment such as catalyst coolers and strippers, resulting in various open volumes of the elements into which catalyst might exist; and design and operating conditions in the various elements of the reactor apparatus, including pressure drops across control (typically slide) valves requiring more or less catalyst in the conduits feeding the valves, desired GSV, rate and type of fluffing vapor (which assists catalyst fluidization) in various elements and lift gas in various conduits, and levels of catalyst in various elements; and base activity of the catalyst prior to introduction to the reactor apparatus and the level of coke on the catalyst in the reaction zone during use in the reactor apparatus, each of which will determine how much catalyst is needed in the reaction zone to achieve a desired conversion of oxygenate feedstock, and the desired level of conversion of oxygenate feedstock.

During the conversion of oxygenates to prime olefins, carbonaceous deposits accumulate on the catalyst used to promote the conversion reaction. At some point, the build up of these carbonaceous deposits causes a reduction in the capability of the catalyst to convert the oxygenate feed to light olefins. At this point, the catalyst is partially deactivated. When a catalyst can no longer convert an oxygenate to an olefin product, the catalyst is considered to be fully deactivated. According to another embodiment of the present invention, a portion of the catalyst is withdrawn from the reactor apparatus and is partially, if not fully, regenerated in a regenerator. By regeneration, it is meant that the carbonaceous deposits are at least partially removed from the catalyst. Desirably, the portion of the catalyst withdrawn from the reactor apparatus is at least partially deactivated. The regenerated catalyst, with or without cooling, is then returned to the reactor apparatus.

Desirably, a portion of the catalyst, comprising molecular sieve and any other materials such as binders, fillers, etc., is removed from the reactor apparatus for regeneration and return back to the reactor apparatus at a rate of from about 0.1 times to about 10 times, more desirably from about 0.2 to about 5 times, and most desirably from about 0.3 to about 3 times the total feed rate of oxygenates to the reaction zone. These rates pertain to the catalyst containing molecular sieve only, and do not include any non-reactive solids which may be present for temperature control purposes. The rate of total solids, i.e., catalyst and non-reactive solids, removed from the reactor apparatus for regeneration and recirculation back to the reactor will vary these rates in direct proportion to the content of non-reactive solids in the total solids.

Desirably, the catalyst regeneration is carried out in the presence of a gas comprising oxygen or other oxidants. Examples of other oxidants include, but are not necessarily limited to, singlet $O_2$, $O_3$, $SO_3$, $N_2O$, NO, $NO_2$, $N_2O_5$, and mixtures thereof. Air and air diluted with nitrogen or $CO_2$ are desired regeneration gases. The oxygen concentration in air can be reduced to a controlled level to minimize overheating of, or creating hot spots in, the regenerator. The catalyst may also be regenerated reductively with hydrogen, mixtures of hydrogen and carbon monoxide, or other suitable reducing gases.

The catalyst may be regenerated in any number of methods: batch, continuous, semi-continuous, or a combination thereof. Continuous catalyst regeneration is a desired method. Desirably, the catalyst is regenerated to a level of remaining coke from about 0.01 wt. % to about 15 wt. % of the weight of the catalyst, more desirably from about 0.1 wt. % to about 10 wt. %, still more desirably from about 0.2 wt. % to about 5 wt. %, and most desirably from about 0.3 wt. % to about 2 wt. %.

The catalyst regeneration temperature should be from about 300° C. to about 800° C., desirably from about 500° C. to about 750° C., and most desirably from about 550° C. to about 720° C. Because the regeneration reaction takes place at a temperature considerably higher than the oxygenate conversion reaction, it may be desirable to cool at least a portion of the regenerated catalyst to a lower temperature before it is sent back to the reactor. A heat exchanger located internal or external to the regenerator may be used to remove some heat from the catalyst after it has been withdrawn from the regenerator. When the regenerated catalyst is cooled externally, it is desirable to cool it to a temperature which is from about 200° C. higher to about 200° C. lower than the temperature of the catalyst withdrawn from the reactor apparatus. More desirably, it is cooled to a temperature from about 100° C. higher to about 200° C. lower than the temperature of the catalyst withdrawn from the reactor apparatus. This cooled catalyst then may be returned to either some portion of the reactor apparatus, the catalyst regenerator or both. When the regenerated catalyst from the regenerator is returned to a reactor apparatus, it may be returned to the disengaging zone, the reaction zone, the catalyst distribution zone and/or the inlet zone. Preferably the regenerated catalyst from the regenerator is returned to the recirculation zone, most preferably to the disengaging zone. Direct or indirect introduction of the cooled catalyst into the reactor or regenerator serves to reduce the average temperature in the reactor or regenerator.

Desirably, catalyst regeneration is carried out on at least partially deactivated catalyst that has been stripped of most of readily removable organic materials (organics) in a stripper or stripping chamber that is part of the reactor apparatus. This stripping can be achieved by passing a stripping gas over the spent catalyst at an elevated temperature. Gases suitable for stripping include steam, nitrogen, helium, argon, methane, $CO_2$, CO, hydrogen, and mixtures thereof. A preferred gas is steam. Gas hourly space velocity (GHSV, based on volume of gas to volume of catalyst and coke) of the stripping gas is from about 0.1 $hr^{-1}$ to about 20,000 $hr^{-1}$. Acceptable temperatures of stripping are from about 250° C. to about 750° C., and desirably from about 350° C. to about 650° C.

Catalyst that has been contacted with feed in a reactor apparatus is defined herein as "feedstock exposed." Feedstock exposed catalyst will provide olefin conversion reaction products having substantially lower propane and coke content than a catalyst which is fresh or regenerated. By "fresh catalyst" is meant catalyst that has not been previously introduced to a reactor apparatus. A catalyst will typically provide lower amounts of propane as it is exposed to more feed, either through increasing time at a given feed rate or increasing feed rate over a given time.

At any given instant in time, some of the catalyst in the reactor apparatus may be fresh, some regenerated, and some coked or partially coked as a result of having not yet been regenerated. Therefore, various portions of the catalyst in the reactor apparatus may have been feedstock exposed for different periods of time. Since the rate at which oxygenate feedstock and catalyst flows to the reactor apparatus can vary, the amount of feed to which various portions of the catalyst have been exposed can also vary. To account for this variation, the "average catalyst feedstock exposure index (ACFE index)" is used to quantitatively define the extent to which the entire catalyst in the reactor apparatus has been feedstock exposed.

As used herein, ACFE index is the total weight of oxygenate feedstock plus optional hydrocarbon feed sent to the reactor apparatus divided by the total weight of fresh and regenerated molecular sieve (i.e., excluding binder, inerts, etc., of the catalyst composition) sent to the reactor apparatus, both total weights measured over the same period of time. The measurement should be made over an equivalent time interval, and the time interval should be long enough to smooth out fluctuations in catalyst or feedstock rates according to the reactor apparatus and regeneration process step selected to allow the system to be viewed as essentially continuous. In the case of reactor systems with periodic regenerations, this can range from hours up to days or longer. In the case of reactor systems with substantially constant regeneration, minutes or hours may be sufficient. By "reactor system" is meant the combination of at least a reactor apparatus and a regenerator, with flow of catalyst between each.

Flow rate of catalyst can be measured in a variety of ways well known to those skilled in the art. In the design of the equipment used to carry the catalyst between the reactor apparatus and regenerator, the catalyst flow rate can be determined given the coke production rate in the reactor apparatus, the average coke level on catalyst leaving the reactor apparatus, and the average coke level on catalyst leaving the regenerator. In an operating unit with continuous catalyst flow, a variety of measurement techniques can be used. Many such techniques are described, for example, by Michel Louge, "Experimental Techniques," *Circulating Fluidized Beds*, Grace, Avidan, & Knowlton, eds., Blackie, 1997 (336–337), the descriptions of which are expressly incorporated herein by reference.

In this invention, only the molecular sieve in the catalyst sent to the reactor apparatus may be used in the determination of ACFE index. The catalyst sent to the reactor apparatus, however, can be either fresh or regenerated or a combination of both. Molecular sieve which may be moved around within the reactor apparatus, for example via the recirculation zone, and which has not been regenerated or does not contain fresh catalyst, is not to be used in the determination of ACFE index. In one embodiment, fresh catalyst may be introduced to the regenerator rather than directly to the reactor apparatus, in which case it becomes indistinguishable from regenerated catalyst from the regenerator, and measurements of rates of catalyst from the regenerator to the reactor apparatus may be sufficient to determine ACFE index along with measurements of rates of oxygenate feedstock and optional hydrocarbon feed. In yet another embodiment, a regenerator may not be employed, and only fresh catalyst may be sent to the reactor apparatus, and thus only measurements of the fresh catalyst to the reactor apparatus may be sufficient determine ACFE index along with measurements of rates of oxygenate feedstock and optional hydrocarbon feed.

In a preferred embodiment of this invention, an oxygenate feedstock, and optionally a hydrocarbon feed, either separately or mixed with the oxygenate, is contacted with a catalyst containing a SAPO molecular sieve at process conditions effective to produce olefins in a reactor apparatus where the catalyst has an ACFE index of at least about 1.0, preferably at least about 1.5, more preferably at least about 2.0. An ACFE index in the range of about 1.0 to about 20 is effective, with a range of about 1.5 to about 15 being desirable. A range of about 2.0 to about 12 is particularly preferred.

The oxygenate conversion reaction products, along with any catalyst decay products, may be separated and purified to produce high purity olefins. High purity olefins are generally recognized by those skilled in the art to contain at least about 80 wt. % olefin of a single carbon number, preferably at least about 90 wt. %, more preferably at least about 95 wt. %, and most desirably at least about 99 wt. %. High purity olefins are also generally recognized as meeting further requirements around what type of components may be present with the desired olefin of a single carbon number. For example, in various embodiments of the present invention one or more products such as high purity ethylene, high purity propylene or high purity butylenes may be produced. In another embodiment of the present invention the high purity butylene product may be further processed to form products comprised of very high concentrations of particular butylene isomers, for example, high purity butene-1 comprising at least about 80 wt. % butene-1, or alternatively at least about 90 wt. % butene-1.

Purification to make high purity olefins traditionally requires removal of low level impurities which interfere with the use of high purity olefins in subsequent derivative manufacture, particularly in the polymerization of ethylene and propylene. Low level contaminants generally comprise polar molecules, including oxygenates such as water, alcohols, carboxylic acids, ethers, and carbon oxides; sulfur compounds such as hydrogen sulfide, carbonyl sulfide and mercaptans; ammonia and other nitrogen compounds; arsine, phosphine; and chlorides. Other contaminants can be hydrocarbons such as acetylene, methyl acetylene, propadiene, butadiene and butyne, among others. Hydrogen is another contaminant of high purity olefin streams.

Low level contaminants can be removed by a variety of processes, including hydrogenation reactions to saturate certain hydrocarbons; acid-base reactions, e.g. caustic washes to remove certain sulfur compounds and carbon dioxide; absorption of certain polar compounds with various materials, such as solid molecular sieves; extraction with various solvents; membrane permeation; and fractional distillation. In addition, the desired olefin of a given boiling point may be separated from a mix of olefins and paraffins of various other boiling points, including paraffins having the same number of carbon atoms as the desired olefin. This can be done using conventional fractional distillation techniques, or also using conventional absorbtion, extraction or membrane separations.

Regardless of the purity of high purity olefins desired, the method of the present invention may be particularly effective at scales (oxygenate feed and prime olefin product rates, with commensurate reactor apparatus volumes) significantly above typical laboratory or bench scale. At scales greater than typical laboratory or bench scale, recovery of high purity olefins, which will benefit from the enhanced conversion of oxygenate feedstock to desired products and the suppression of conversion to undesirable byproducts, may be more desirable. In one embodiment, the prime olefin product generated using the method of the present invention is at least about 5 kg per day. In alternative embodiments, the prime olefin product generated using the method of the present invention is any one of the following: at least about 4,500 kg per day; at least about 500,000 kg per day; at least about 1,000,000 kg per day; at least about 1,300,000 kg per day; at least about 1,900,000 kg/day; and at least about 2,700,000 kg per day.

One skilled in the art will also appreciate that the olefins produced by the oxygenate-to-olefin conversion reaction of the present invention, particularly the high purity olefins, can be polymerized to form polyolefins, particularly polyethylene and polypropylene. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst. The preferred temperature range of operation is between 50 and 240° C. and the reaction can be carried out at low, medium or high pressure, being anywhere within the range of about 1 to 200 bars. For processes carried out in solution, an inert diluent can be used, and the preferred operating pressure range is between 10 and 150 bars, with a preferred temperature range of between 120 and 230° C. For gas phase processes, it is preferred that the temperature generally be within a range of 60 to 160° C., and that the operating pressure be between 5 and 50 bars.

In addition to polyolefins, numerous other olefin derivatives may be formed from the olefins recovered therefrom, including high purity olefins. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

DETAILED DESCRIPTION OF THE DRAWINGS

Figure 2:
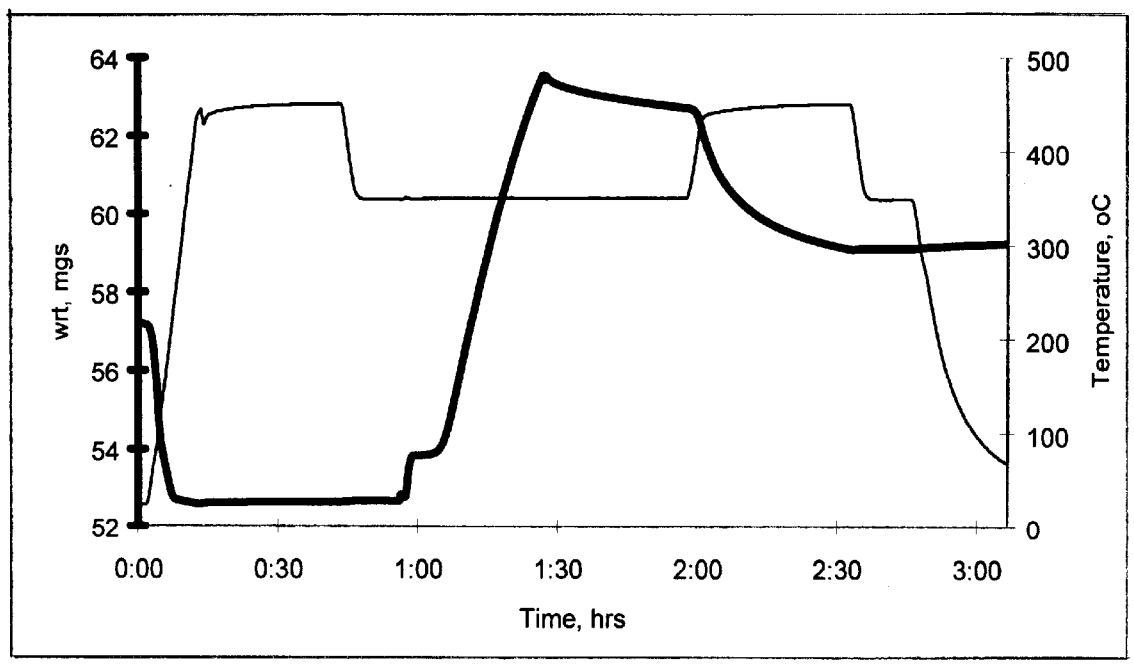
FIG. 2 is a graph of the results of a thermogravimetric analysis of an oxygenate conversion reaction at 350° C. and exposure of the molecular sieve utilized to various temperatures.
Figure 3:
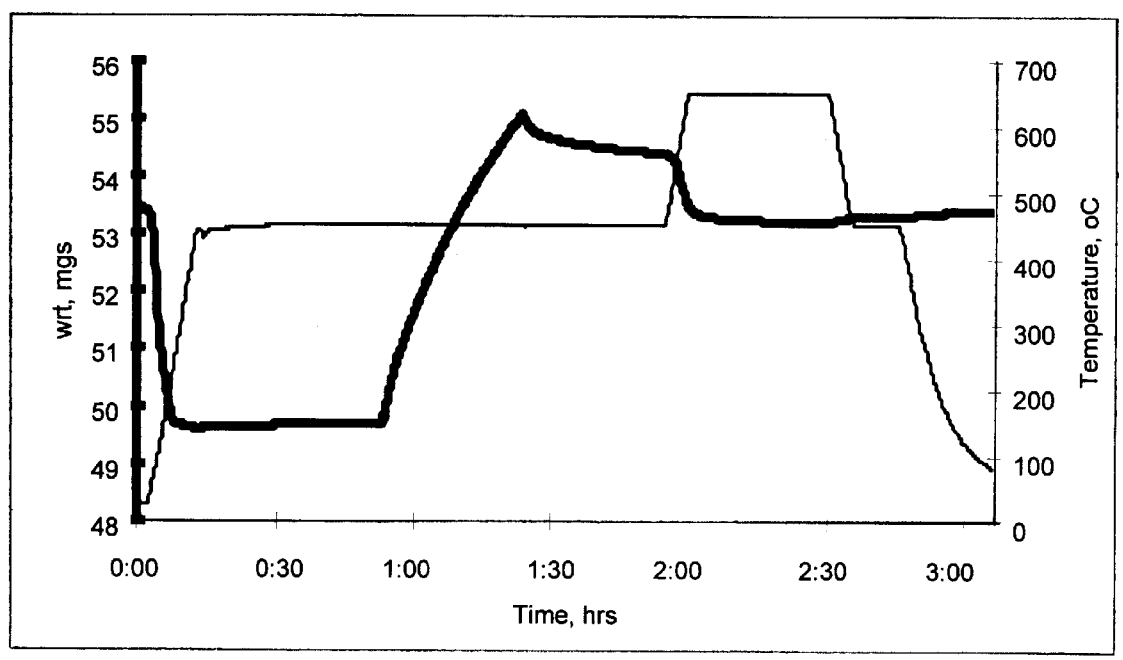
FIG. 3 is a graph of the results of a thermogravimetric analysis of an oxygenate conversion reaction at 450° C. and exposure of the molecular sieve utilized to various temperatures.

FIGS. 1 through 3 provide the results of three examples (Examples 1–3 below) of thermogravimetric analysis (TGA) of a catalyst while conducting an oxygenate conversion reaction at various temperatures, and then subsequently ceasing the oxygenate conversion reaction and leaving the catalyst exposed at various suboptimum conditions.

53 to 59 grams of as synthesized, template containing SAPO-34 catalyst prepared according to the method of U.S. Pat. No. 4,440,871 to Lok, et. al., were loaded into a standard Cahn Model 121 TGA, which measures the weight of the catalyst as it undergoes exposure to any desired atmosphere and under controllable temperatures within the device, indicated by the thick line according to the scale on the left hand side of the figures. The thin line indicates the temperature of the catalyst and the environment inside the TGA according to the scale on the right hand side of the figures. The weight and temperature conditions are shown for the same point in time according to the scale at the bottom of the figures, and the changes are shown across the time period of the experiment.

In each example, the SAPO-34 molecular sieve was ramped up from ambient to a temperature of about 450° C. in the presence of 50 standard cubic centimeters per minute (scc/min) of flowing pure helium in about 10 minutes, and then left at that temperature under the same flow of helium for another approximately 40 minutes to drive off any previously adsorbed species from the molecular sieve and to activate it for oxygenate conversion. The drop in the weight of the molecular sieve during the start of the experiment shows the removal of the adsorbed materials from the molecular sieve. The temperature was then changed to that desired to conduct an oxygenate conversion reaction.

After activation and reaching the desired temperature in the TGA instrument, the flow of pure helium was ceased and replaced with a blend of methanol vapor and helium generated by passing 50 scc/min helium through a methanol liquid containing bubbler at ambient temperature, and an oxygenate conversion reaction commenced at the temperature in the TGA instrument, which continued for some time. As shown in FIGS. 1–3, the molecular sieve gains weight due to absorption of the oxygenate feedstock (or oxygenate conversion products as the oxygenate is transformed within the molecular sieve) and from the carbonaceous deposits formed. At some point, the methanol feed is terminated and replaced with flowing pure helium at the rate noted above, and the temperature is left at the same level at which the oxygenate conversion reaction was conducted for some period of time, then raised to some level for another period of time, and finally reduced back to room temperature for removal and examination of the molecular sieve. In each example, the oxygenate utilized was US Grade AA methanol, the partial pressure of methanol was about 19.8 kPa and the total reactor pressure was about 110 kPa.

Figure 4:
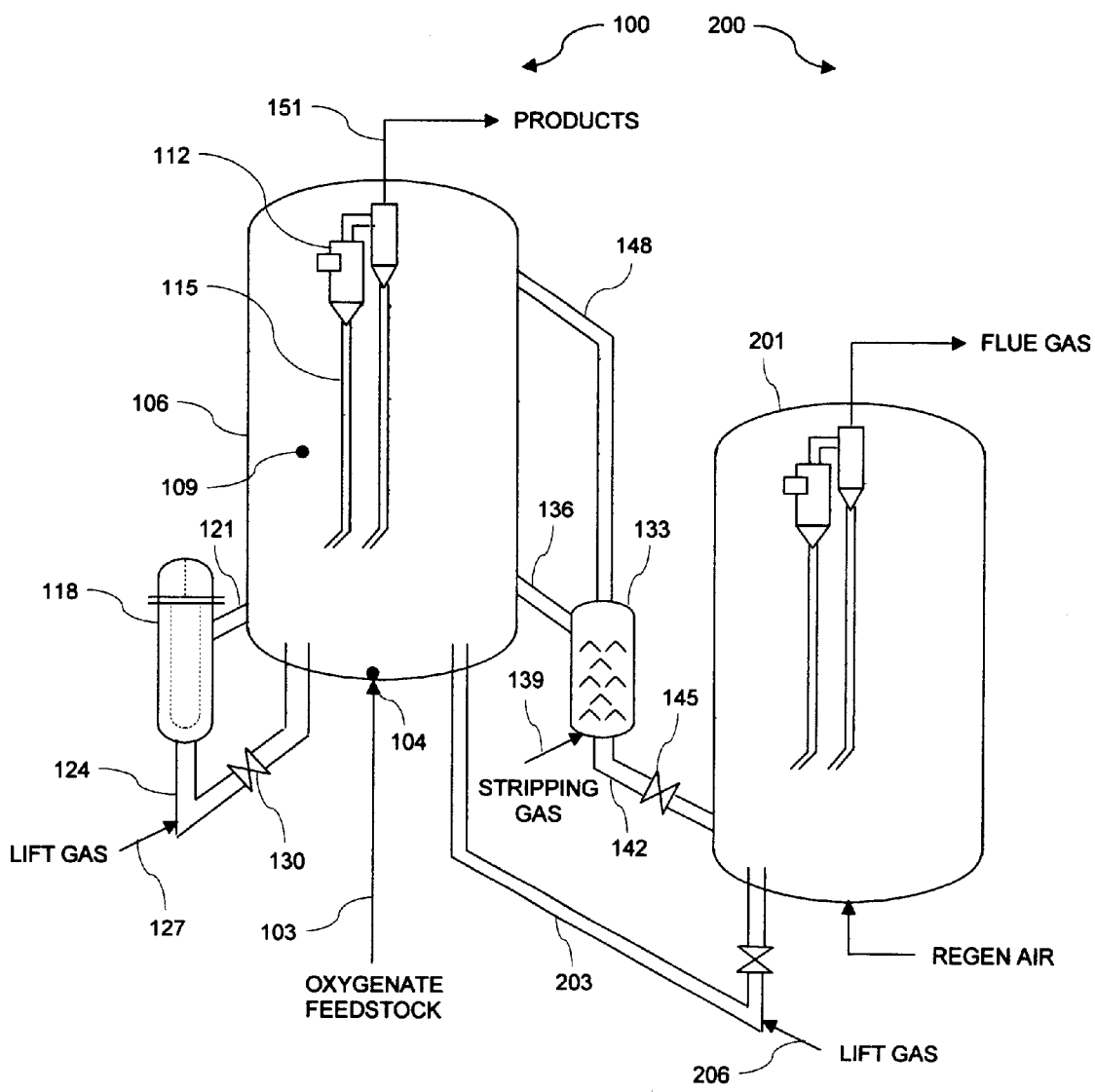
FIG. 4 is a schematic of an embodiment of a reactor apparatus of the present invention.

FIG. 4 is a schematic diagram representing an embodiment of a reactor apparatus 100 utilizing the method of the present invention in conjunction with a catalyst regenerator 200. Oxygenate feedstock, comprising at least some in a vaporized form, is supplied through line 103 to a reactor vessel 106, the reactor vessel including a reaction zone 109 comprising an inlet zone 104, containing fluidizable SAPO bearing catalyst particles. An oxygenate conversion reaction takes place in and products including prime olefins are formed in the reaction zone 109, and a portion of the fluidizable particles are carried into the cyclone separator device 112, which comprises one element of the recirculation zone, and is the first element of the disengaging zone that eventually leads to products leaving the reactor apparatus altogether (through line 151). In cyclone separator device 112, catalyst is largely separated from the oxygenate conversion products, and any diluent or unconverted oxygenate feedstock that may be present, and falls into dipleg 115, where it is transferred back into reaction zone 109. Further, catalyst also flows from reaction zone 109 into a catalyst heat exchanger 118, typically by gravity via a line 121. Catalyst may flow from heat exchanger 118 typically by gravity into a line 124, into which a lift gas is introduced by line 127 to cause the catalyst to flow against gravity back into reaction zone 109. Optionally, a control valve 130 may be used, and may be placed before or after the introduction of lift gas on the way to reaction zone 109. Further, catalyst may also flow from reaction zone 109 into a catalyst stripper 133, typically by gravity via a line 136. Catalyst stripper 133 may contain various elements to enhance the stripping action, such as trays, typically shed trays and other elements well known to those skilled in the art. A stripping gas may be introduced via line 139 into the catalyst stripper 133 to enhance removal of entrained oxygenate conversion products and any unreacted oxygenate feedstock from the catalyst prior to sending the catalyst to catalyst regenerator vessel 201, typically by gravity via line 142. Optionally, a control valve 145 may be used in line 142. Gaseous materials from catalyst stripper 133 may be returned to reaction zone 109 via line 148. Regenerated catalyst may be returned to reaction zone 109 via a line 203, utilizing lift gas from a line 206. Oxygenate conversion products from the oxygenate conversion reaction in reaction zone 109, and any catalyst decay products from the recirculation zone, and any unconverted oxygenate feedstock are removed from the reactor apparatus in line 151. Some small measure of such materials may be introduced into the regenerator 200 due to the imperfect nature of stripping in catalyst stripper 133.

In the embodiment shown in FIG. 4, the recirculation zone of the reactor apparatus would comprise elements 112, 115, 118, 121, 124, 130, 133, 136, 142 and 145, catalyst decay would occur in those elements and catalyst decay products would emanate from those elements into the reaction zone. A determination of the mass of catalyst within those elements would be made, in order to develop the appropriate ratio including the mass of catalyst in the reaction zone 109, which includes inlet zone 104.

Figure 5:
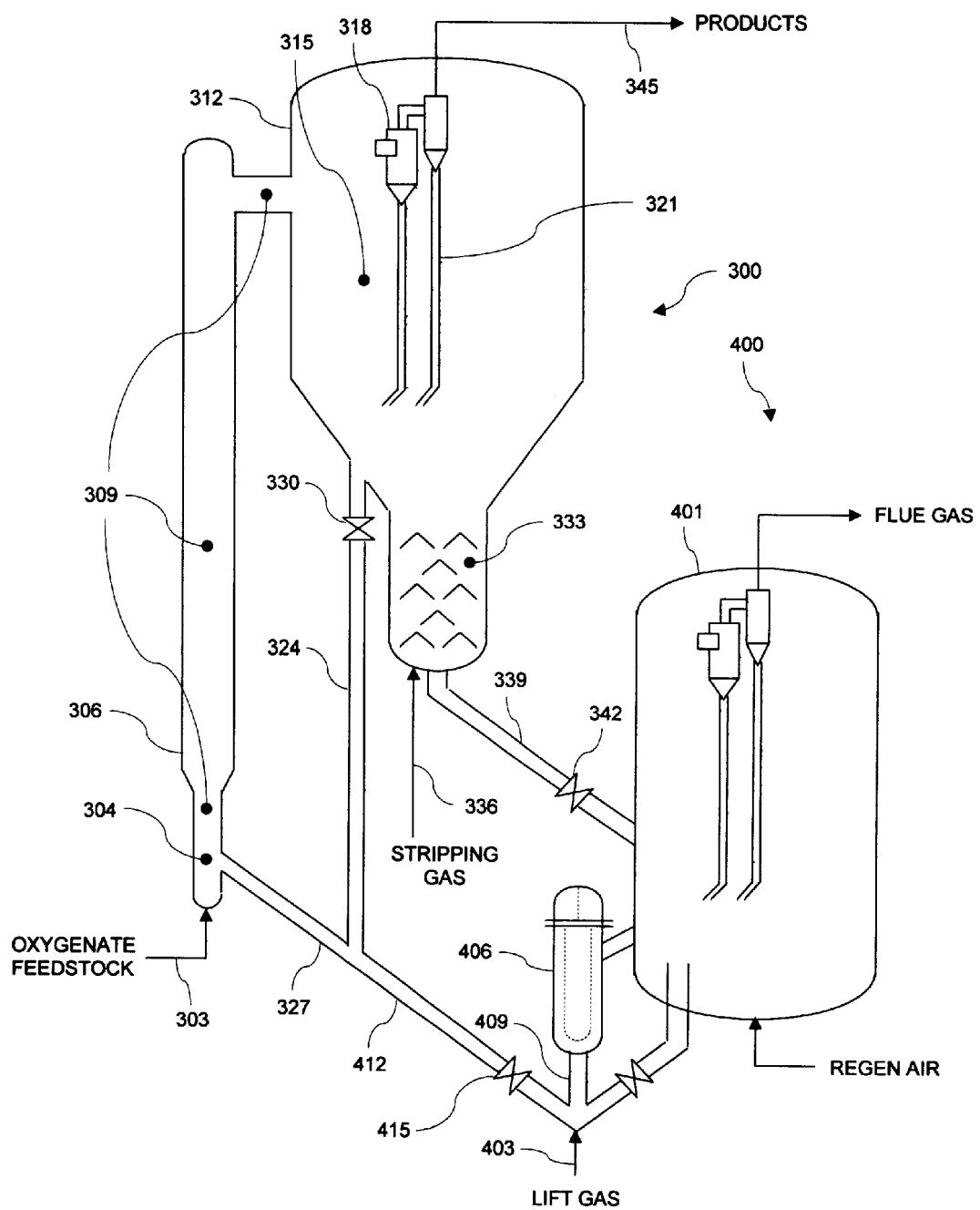
FIG. 5 is a schematic of another embodiment of a reactor apparatus of the present invention.

FIG. 5 is a schematic diagram of another embodiment of a reactor apparatus 300 utilizing the method of the present invention in conjunction with a catalyst regenerator 400. Oxygenate feedstock, comprising at least some in a vaporized form, is supplied through line 303 to a reactor vessel 306, the reactor vessel including a reaction zone 309 comprising an inlet zone 304, containing fluidizable SAPO bearing catalyst particles. An oxygenate conversion reaction takes place in and products including prime olefins are formed in reaction zone 309, and a portion of the fluidizable particles are carried into termination vessel 312, comprising a termination vessel volume 315, which is one element of the recirculation zone, and is the first element of the disengaging zone that eventually leads to products leaving the reactor apparatus altogether (through line 345). Termination vessel volume 315 is of substantially larger cross sectional area than the reaction zone, thus significantly slowing the GSV in that termination space and allowing a large portion of the catalyst to settle downward with gravity and become largely separated from the oxygenate conversion products, and any diluent or unconverted oxygenate conversion feedstock that may be present. Another portion of the fluidizable catalyst particles are carried into a cyclone separator device 318, where catalyst is also largely separated from the oxygenate conversion products, and any diluent or unconverted oxygenate conversion feedstock that may be present, and falls into dipleg 321, where it is transferred into termination vessel volume 315. A portion of the catalyst from termination vessel volume 315 may flow into catalyst recirculation line 324, and subsequently into line 327 where it joins catalyst coming from the regenerator 400, and both types of catalyst are lifted against gravity with lift gas 403 to enter inlet zone 304. Optionally, a control valve 330 may be used on catalyst recirculation line 324. Another portion of the catalyst from termination vessel volume 315 may flow into a catalyst stripper 333, which in this example is also contained within termination vessel 312. Catalyst stripper 333 may contain various elements to enhance the stripping action, such as trays, typically shed trays and other elements well known to those skilled in the art. A stripping gas may be introduced via line 336 into the catalyst stripper 333 to enhance removal of entrained oxygenate conversion products and any unconverted oxygenate feedstock from the catalyst prior to sending the catalyst to catalyst regenerator vessel 401, typically by gravity via line 339. Optionally, a control valve 342 may be used in line 339. Gaseous materials may flow up from catalyst stripper 333 into termination vessel volume 315. Regenerated catalyst may be returned to inlet zone 304, in this example after having been cooled in catalyst cooler 406, passing through a line 409 in fluid communication with another line 412, and joining with the catalyst being recirculated through the termination vessel volume in line 327. Optionally, a control valve 415 may be used in line 412. Oxygenate conversion products from the oxygenate conversion reaction in reaction zone 309, and any catalyst decay products from the recirculation zone, and any unconverted oxygenate feedstock are removed from the reactor apparatus in line 345. Some small measure of such materials may be introduced into the regenerator 400 due to the imperfect nature of stripping in catalyst stripper 333.

In the embodiment shown in FIG. 5, the recirculation zone comprises elements 315, 318, 321, 324, 327, 330, 333, 339 and 341, and a determination of the mass of catalyst within those elements would be made, in order to develop the appropriate ratio including the mass of catalyst in the reaction zone 309, which includes inlet zone 304.

This invention will be better understood with reference to the following examples, which are intended to illustrate specific embodiments within the overall scope of the invention as claimed.

EXAMPLE 1

Referring to FIG. 1, the methanol conversion reaction is conducted at 250° C. beginning at about 1:00 hours into the experiment and is continued for approximately 30 minutes. In the first roughly 5 minutes, the molecular sieve gains weight quite quickly primarily through absorption of the feedstock, and thereafter gains weight quite slowly through the formation of carbonaceous deposits (which occurs slowly at the relatively low temperature of 250° C.). At about 1:30 hours after commencing the experiment, methanol is stopped and replaced with flowing helium while maintaining the environment at the same 250° C. Weight loss commences immediately through about 2:00 hours, at which point further weight loss slows has about stopped, and the molecular sieve has lost over 80% of the weight it gained while being exposed to methanol. At about 2:00 hours, while still under flowing helium, the temperature is quickly raised to 450° C., and the molecular sieve again continues to lose weight until about 2:30 hours, at which point it has lost over 95% of the weight it gained under the oxygenate conversion reaction. The TGA is then cooled to ambient temperature.

EXAMPLE 2

Referring to FIG. 2, the experiment described in Example 1 is repeated, except that the oxygenate conversion reaction is conducted at 350° C. The catalyst gains about 10.7 mg of weight over the half hour the catalyst is exposed to methanol. It then loses about 7% of that weight gain over the next half hour exposed to flowing helium at the oxygenate conversion reaction temperature, and loses an additional 30% when the temperature is increased to 450° C.

EXAMPLE 3

Referring to FIG. 3, the experiment described in Example 1 is repeated, except that the oxygenate conversion reaction is conducted at 450° C., and the temperature is increased to 650° C. at the 2:00 hour mark. The catalyst gains about 5.3 mg of weight over the thirty minutes the catalyst is exposed to methanol. After termination of methanol flow and establishing the pure helium flow, it then loses over 10% of that weight gain over the next half hour exposed to flowing helium at the oxygenate conversion reaction temperature, and loses an additional 20% when the temperature is increased to 650° C.

Examples 1 through 3 above clearly demonstrate the newly discovered phenomena of how a SAPO molecular sieve catalyst, having been utilized in an oxygenate conversion reaction, undergoes a transformation during exposure to temperature in the substantial absence of oxygenate feedstock. This transformation includes a significant loss of weight that the catalyst acquired during the oxygenate conversion reaction. If further shows how that loss of weight is increased by increasing temperature above that at which the oxygenate conversion reaction is originally conducted.

EXAMPLE 4

A fluidized bed reactor apparatus resembling that described as FIG. 5, further comprising a regenerator as shown in FIG. 5, is employed in an oxygenate conversion reaction process of the present invention, with the exception that there is no line 324, catalyst heat exchanger 406 or line 409. Thus all catalyst flows from catalyst stripper 333 to the regenerator vessel 401 and is returned from there to inlet zone 304. In this apparatus is placed 1.5 kg of catalyst comprising 25% SAPO-34 molecular sieve prepared according to the method of U.S. Pat. No. 4,440,871 to Lok, et. al. The reactor apparatus is designed and operated such that about about 50 grams of catalyst is contained within the reaction zone during an oxygenate conversion reaction, and the balance in the recirculation zone. Thus, the ratio of the mass of catalyst in the reaction zone to that of the sum of the mass of catalyst in both the reaction zone and the recirculation zone is about 0.03. 0.8 kg/hr of 100% vaporized US Grade AA methanol is introduced to inlet zone 304 at a temperature of about 160° C. An oxygenate conversion reaction is conducted at a WHSV in the reaction zone of about 15 hr$^{-1}$, a temperature of about 450° C., and a pressure of about 240 kPa. The GSV in the reaction zone is about 3 m/s, and the conversion of oxygenate across the reactor apparatus is about 90%. The reactor apparatus is covered with heating elements and insulation such that all elements of the recirculation zone are kept at about the same temperature as the reaction zone. The catalyst is regenerated by exposure to air at a temperature of about 625° C., and the regenerator is designed and operated such that the regenerator contains another about 1.5 kg catalyst (thus, the total amount of catalyst in both the reactor apparatus and the regenerator is about 3.0 kg). Samples of the gaseous oxygenate conversion product, any diluents and any unconverted oxygenate feedstock are taken on a Supelco petrocol DB-150 chromatograph at three different points: a) just before exiting the reaction zone 309 and entering the termination vessel 315, b) at the top of the level of catalyst within stripper 333, and c) exiting the reactor apparatus in line 345. The results are provided in Table 1, which exclude any water and diluents that may be present.

TABLE 1

| Sample Point | a | b | c |
|---|---|---|---|
| Rate Hydrocabon plus Unconverted Methanol (kg/hr) | 0.298 | 0.040 | 0.338 |
| Hydrocarbon Composition (selectivity wt. %) | | | |
| Ethylene | 18.9 | 6.58 | 18.1 |
| Propylene | 42.3 | 11.5 | 36.7 |
| Methane + Ethane | 3.19 | 4.47 | 3.57 |
| Propane | 3.15 | 28.4 | 8.11 |
| C4s | 16.8 | 23.3 | 16.8 |
| C5+ | 15.6 | 25.1 | 16.6 |

EXAMPLE 5

A fluidized bed reactor apparatus similar to that described as FIG. 5, further comprising a regenerator as shown in FIG. 5, is employed in an oxygenate conversion reaction process of the present invention, with the exception that there is no catalyst heat exchanger 406 or line 409. Thus some catalyst flows from catalyst stripper 333 to the regenerator vessel 401 and is returned from there to inlet zone 304, while some flows through line 324 and is returned to inlet zone 304 without regeneration. In this apparatus is placed about 100 kg of catalyst comprising 25% SAPO-34 molecular sieve prepared according to the method of U.S. Pat. No. 4,440,871 to Lok, et. al. The reactor apparatus is designed and operated such that about 36 kg of catalyst is contained within the reaction zone during an oxygenate conversion reaction, and the balance in the recirculation zone. Thus, the ratio of the mass of catalyst in the reaction zone to that of the sum of the mass of catalyst in both the reaction zone and the recirculation zone is about 0.36. 550 kg/hr of about 95% vaporized US Grade AA methanol is introduced to inlet zone 304 at a temperature of about 110° C., and a pressure of about 450 kPa. An oxygenate conversion reaction is conducted at a WHSV in the reaction zone of 15 hr$^{-1}$, a temperature of about 490° C., and a pressure of about 275 kPa. The GSV in the reaction zone is about 6.5 m/s, and the conversion of oxygenate across the reactor apparatus is about 98%. The reactor apparatus is covered with heating elements and insulation such that all elements of the recirculation zone are kept at about the same temperature as the reaction zone. About 96% of the catalyst flowing through reaction zone 309 and into termination vessel volume 315 is sent through lines 324 and 327 back into inlet zone 304, and the balance is sent to the regenerator vessel 401 via line 339, regenerated and returned to inlet zone 304 via lines 412 and 327. The catalyst is regenerated by exposure to air at a temperature of 685° C., and the regenerator is designed and operated such that the regenerator contains another about 200 kg catalyst (thus, the total amount of catalyst in both the reactor apparatus and the regenerator is about 300 kg). Samples of the gaseous oxygenate conversion product, any diluents and any unconverted oxygenate feedstock are taken on a Supelco petrocol DB-150 chromatograph column to determine gas phase hydrocarbon and oxygenate compositions at three different points: a) just before exiting the reaction zone 309 and entering the termination vessel 315, b) at the top of the level of catalyst within stripper 333, and c) exiting the reactor apparatus in line 345. The results are provided in Table 2, which exclude any water and diluents that may be present.

TABLE 2

| Sample Point | a | b | c |
|---|---|---|---|
| Rate Hydrocabon plus Unconverted Methanol (kg/hr) | 235 | 14.2 | 249 |
| Hydrocarbon Composition (selectivity wt. %) | | | |
| Ethylene | 36.7 | 26.2 | 35.6 |
| Propylene | 39.8 | 31.3 | 39.4 |
| Methane + Ethane | 2.04 | 5.67 | 2.37 |
| Propane | 2.77 | 8.43 | 3.46 |
| C4s | 12.5 | 14.8 | 12.8 |
| C5+ | 6.19 | 13.6 | 6.37 |

Examples 4 and 5 clearly show the detrimental impact of the catalyst decay phenomena which occurs with SAPO catalysts in the process of conducting an oxygenate conversion reaction in a fluidized bed apparatus. It is evident that the weight loss of the catalyst shown in Examples 1 through 3 above is manifested in the production of gaseous catalyst decay products of a substantially inferior composition to that obtained in the reaction zone under desired oxygenate conversion reaction conditions, viewed through the data obtained for the composition from sample point (b) relative to the composition from sample point (a) in Examples 4 and 5 above. Additionally, it is shown that increasing the ratio of the mass of catalyst in the reaction zone to that of the sum of the mass of catalyst in both the reaction zone and the recirculation zone may improve the product quality and prime olefin yield of the overall production from an oxygenate conversion reaction in a fluidized bed reactor apparatus.

Having now fully described this invention, it will be appreciated by those skilled in the art that the invention can be performed within a wide range of parameters within what is claimed, without departing from the scope and spirit of the invention.

We claim:

1. A method for conducting an oxygenate conversion reaction in a fluidized bed reactor comprising:
   providing an oxygenate feedstock, a catalyst that incorporates a SAPO molecular sieve, and a reactor apparatus including at least a reaction zone and a recirculation zone, wherein the temperature in at least one point in each of said reaction zone and said recirculation zone is about 250° C. or greater;
   contacting said feedstock wit said catalyst in said reaction zone under conditions effective to convert said feedstock to a product including prime olefins, said conditions including a GSV of about 0.1 m/s or greater at at least one point in said reaction zone;
   recirculating at least a portion of said catalyst in said reaction zone flow through said recirculation zone such that a ratio of the mass of said catalyst in said reaction zone to that of the sum of the mass of said catalyst in both said reaction zone and said recirculation zone is from 0.30 to 0.99.

2. A The method of claim 1 wherein the ratio of the mass of catalyst in said reaction zone to that of the sum of the mass of catalyst in both said reaction zone and said recirculation zone is from about 0.40 to 0.99.

3. The method of claim 1 wherein the ratio of the mass of catalyst in said reaction zone to that of the sum of the mass of catalyst in both said reaction zone and said recirculation zone is from about 0.50 to 0.99.

4. The method of claim 1 wherein the ratio of the mass of catalyst in said reaction zone to that of the sum of the mass of catalyst in both said reaction zone and said recirculation zone is from about 0.30 to about 0.98.

5. The method of claim 1 wherein the ratio of the mass of catalyst in said reaction zone to that of the sum of the mass of catalyst in both said reaction zone and said recirculation zone is from about 0.40 to about 0.98.

6. The method of claim 1 wherein the ratio of the mass of catalyst in said reaction zone to that of the sum of the mass of catalyst in both said reaction zone and said recirculation zone is from about 0.50 to about 0.98.

7. The method of claim 1 wherein the ratio of the mass of catalyst in said reaction zone to that of the sum of the mass of catalyst in both said reaction zone and said recirculation zone is from about 0.30 to about 0.95.

8. The method of claim 1 wherein the ratio of the mass of catalyst in said reaction zone to that of the sum of the mass of catalyst in both said reaction zone and said recirculation zone is from about 0.40 to about 0.95.

9. The method of claim 1 wherein the ratio of the mass of catalyst in said reaction zone to that of the sum of the catalyst of catalyst in both said reaction zone and said recirculation zone is from about 0.50 to about 0.95.

10. The method of claim 7 further wherein said temperature in at least one point in each of said reaction zone and said recirculation zone is no greater than about 750°.

11. The method of claim 10 wherein said conditions include a GSV of about 0.5 m/s or greater at at least one point in said reaction zone.

12. The method of claim 11 further comprising a WHSV in said reaction zone of from about 1 hr$^{-1}$ to about 5000 hr$^{-1}$.

13. The method of claim 10 wherein said conditions include a GSV of at least about 1.0 m/s or greater at at least one point in said reaction zone.

14. The method of claim 10 wherein said conditions include a GSV of about 2.0 m/s or greater at at least one point in said reaction zone.

15. The method of claim 10 wherein said conditions include a GSV of about 2.5 m/s or greater at at least one point in said reaction zone.

16. The method of claim 10 further comprising a WHSV in said reaction zone from about 1 hr$^{-1}$ to about 5000 hr$^{-1}$.

17. The method of claim 7 wherein said temperature in at least one point in each of said reaction zone and said recirculation zone is about 300° C. or greater.

18. The method of claim 7 wherein said temperature in at least one point in each of said reaction zone and said recirculation zone is about 350° C. or greater.

19. The method of claim 18 further wherein the temperature in at least one point in each of said reaction zone and said recirculation zone is about 750° C. or less.

20. The method of claim 18 further wherein the temperature in at least one point in each of said reaction zone and said recirculation zone is about 650° C. or less.

21. The method of claim 20 wherein said conditions include a GSV of about 0.5 m/s or greater at at least one point in said reaction zone.

22. The method of claim 10 wherein said conditions include a GSV of about 0.5 m/s or greater at at least one point in said reaction zone.

23. The method of claim 20 wherein said conditions include a GSV of about 1.0 m/s or greater at at least one point in said reaction zone.

24. The method of claim 20 wherein said conditions include a GSV of about 2.0 m/s or greater at at least one point in said reaction zone.

25. The method of claim 20 wherein said conditions include a GSV of at least about 2.5 m/s or greater at at least one point in said reaction zone.

26. The method of claim 2 further comprising a WHSV in said reaction zone from about 1 hr$^{-1}$ to about 5000 hr$^{-1}$.

27. The method of claim 7 wherein said conditions include a GSV of about 0.5 m/s or greater at at least one point in said reaction zone.

28. The method of claim 27 further comprising a WHSV in said reaction zone of from about 1 hr$^{-1}$ to about 5000 hr$^{-1}$.

29. The method of claim 7 wherein said conditions include a GSV of about 1.0 m/s at at least one point in said reaction zone.

30. The method of claim 7 wherein said conditions include a GSV of about 2.0 m/s or greater at at least one point in said reaction zone.

31. The method of claim 7 wherein said conditions include a GSV of about 2.5 m/s or greater at at least one point in said reaction zone.

32. The method of claim 7 further comprising a WHSV in said reaction zone from about 1 hr$^1$ to about 5000 hr$^{-1}$.

33. The method of claim 7 further comprising an oxygenate conversion in the reactor apparatus of about 99% or less.

34. The method of claim 33 further comprising a WHSV in said reaction zone of from about 1 hr$^{-1}$ to about 5000 hr$^{-1}$.

35. The method of claim 7 further comprising an oxygenate conversion in the reactor apparatus of about 98% or less.

36. A method for conducting an oxygenate conversion reaction in a fluidized bed reactor comprising:
providing an oxygenate feedstock, a catalyst that incorporates a SAPO molecular sieve, and a reactor apparatus including at least a reaction zone and a recirculation zone, wherein the temperature in at leapt one point in each of said reaction zone and said recirculation zone is about 250° C. or greater;
contacting said feedstock with said catalyst in said reaction zone under conditions effective to convert said feedstock to a product including prime olefins, said conditions Including a GSV of greater than about 0.5 m/s at at least one point in said reaction zone;
recirculating said catalyst through the recirculation zone to establish a temperature differential, and;
maintaining a ratio of the mass of said catalyst in said reaction zone to that of the sum of the mass of said catalyst in both said reaction zone and said recirculation zone of from 0.30 to 0.99.

37. The method of claim 36 wherein said temperature differential is about 150° C. or less.

38. The method of claim 37 wherein said conditions include a GSV of about 2.0 m/s or greater at at least one point in said reaction zone.

39. The method of claim 37 wherein said conditions includes GSV of about 2.5 m/s or greater at at least one point in said reaction zone.

40. The method of claim 37 wherein said conditions include a GSV of about 4.0 m/s or greater at at least one point in said reaction zone.

41. The method of claim 36 wherein said temperature differential is about 100° C. or less.

42. The method of claim 41 wherein said conditions include a GSV of about 1.0 m/s or greater at at least one paint in said reaction zone.

43. The method of claim 41 wherein said conditions include a GSV of about 2.0 m/s or greater at at least one point in said reaction zone.

44. The method of claim 41 wherein said conditions include a GSV of about 2.5 m/s or greater at at least one point in said reaction zone.

45. The method of claim 41 wherein said conditions include a GSV of about 4.0 m/s or greater at at least one point in said reaction zone.

46. The method of claim 36 wherein said temperature differential is about 50° C. or less.

47. The method of claim 46 wherein said conditions include a GSV of about 1.0 m/s or greater at at least one point in said reaction zone.

48. The method of claim 46 wherein said conditions include a GSV of about 2.0 m/s or greater at at least one point in said reaction zone.

49. The method of claim 46 wherein said conditions include a GSV of about 2.5 m/s or greater at at least one point in said reaction zone.

50. The method of claim 46 wherein said conditions include a GSV of about 4.0 m/s or greater at at least one point in said reaction zone.

51. The method of claim 36 wherein said temperature differential is about 20° C. or less.

52. The method of claim 51 wherein said conditions include a GSV of about 1.0 m/s or greater at at least one point in said reaction zone.

53. The method of claim 51 wherein said conditions include a GSV of about 2.0 m/s or greater at at least one point in said reaction zone.

54. The method of claim 51 wherein said conditions include a GSV of about 2.5 m/s or greater at at least one point in said reaction zone.

55. The method of claim 51 wherein said conditions include a GSV of about 4.0 m/s or greater at at least one point in said reaction zone.

56. The method of claim 36 said conditions include a GSV of about 1.0 m/s or greater at at least one point in said reaction zone.

57. The method of claim 36 wherein said conditions include a GSV of about 2.0 m/s or greater at at least one point in said reaction zone.

58. The method of rein said conditions include a GSV of about 2.5 m/s or greater at at least one point in said reaction zone.

59. The method of claim 36 wherein said conditions include a GSV of about 4.0 m/s or greater at at least one point in said reaction zone.

60. The method of claim 36 wherein the ratio of the mess of catalyst in said reaction zone to that of the sum of the mass of catalyst in both said reaction zone and said recirculation zone of from about 0.40 to 0.99.

61. The method of claim 36 wherein the ratio of the mass of catalyst in said reaction zone to that of the sum of the mess of catalyst in both said reaction zone and said recirculation zone of from about 0.50 to 0.99.

62. The method of claim 36 wherein the ratio of the mass of catalyst in said reaction zone to that of the sum of the mass of catalyst in born said reaction zone and said recirculation zone of from about 0.30 to about 0.98.

63. The method of claim 36 wherein the ratio of the mass of catalyst in said reaction zone to that of the sum of the mass of catalyst in both said reaction zone and said recirculation zone of from about 0.40 to about 0.98.

64. The method of claim 36 wherein the ratio of the mass of catalyst in said reaction zone to that of the sum of the mass of catalyst in both said reaction zone and said recirculation zone of from about 0.50 to about 0.98.

65. The method of claim 36 wherein the ratio of the mass of catalyst in said reaction zone to that of the sum of the mass of catalyst In both said reaction zone and said recirculation zone of from about 0.30 to about 0.95.

66. The method of claim 36 wherein the ratio of the mass of catalyst in said reaction zone to that of the sum of the mass of catalyst in both said reaction zone and said recirculation zone of from about 0.40 to about 0.95.

67. The method of claim 36 wherein the ratio of the mass of catalyst in said reaction zone to that of the sum of the mass of catalyst in both said reaction zone and said recirculation zone of from about 0.50 to about 0.95.

68. The method of claim 37 wherein said conditions include a GSV of about 1.0 m/s or greater at at least one point in said reaction zone.

69. A method for conducting an oxygenate conversion reaction in a fluidized bed reactor comprising:
providing an oxygenate feedstock, a catalyst that incorporates a SAPO molecular sieve, and a reactor apparatus including at least a reaction zone and a recirculation zone, wherein the temperature in at least one point in each of said reaction zone and said recirculation zone is about 250° C. or greater;
contacting said feedstock with said catalyst in said reaction zone under conditions effective to convert said feedstock to a product including prime olefins, said conditions including a GSV of about 0.1 m/s or greater at at least one point in said reaction zone;

having an ACFE index in said reactor apparatus of about 1.0 or greater, and;

having a ratio of the mass of said catalyst in said reaction zone to that of the sum of the mass of said catalyst in both said reaction zone and said recirculation zone of between at least 0.30 to 0.99.

70. The method of claim 69 having an ACFE index of about 1.5 or greater.

71. The method of claim 70 wherein said conditions include a GSV of about 0.5 m/s or greater at at least one point in said reaction zone.

72. The method of claim 70 wherein said conditions include a GSV of about 1.0 m/s or greater at at least one point in said reaction zone.

73. The method of claim 70 wherein said conditions include a GSV of about 2.0 m/s or greater at at least one point in said reaction zone.

74. The method of claim 70 wherein said conditions include a GSV of about 2.5 m/s or greater at at least one point in said reaction zone.

75. The method of claim 70 wherein said conditions include a GSV of about 4.0 m/s or greater at at least one point in said reaction zone.

76. The method of claim 69 having en ACFE index of about 2.0 or greater.

77. The method of claim 76 wherein said conditions include a GSV of about 0.5 m/s or greater at at least one point in said reaction zone.

78. The method of claim 76 wherein said conditions include a GSV of about 1.0 m/s or greater at at least one point in said reaction zone.

79. The method of claim 76 wherein said conditions include a GSV of about 2.0 m/s or greater at at least one point In said reaction zone.

80. The method of claim 76 wherein said conditions include a GSV of about 2.5 m/s or greater at at least one point in said reaction zone.

81. The method of claim 76 wherein said conditions Include a GSV of about 4.0 m/s or greeter at at least one point in said reaction zone.

82. The method of claim 69 wherein said conditions include a GSV of about 0.5 m/s or greater at at least one point in said reaction zone.

83. The method of claim 69 wherein said conditions include a GSV of about 1.0 m/s or greater at at least one point in said reaction zone.

84. The method of claim 69 wherein said conditions include a GSV of about 2.0 m/s or greater at at least one point in said reaction zone.

85. The method of claim 69 wherein said conditions include a GSV of about 2.5 m/s or greaterat at least one point in said reaction zone.

86. The method of claim 69 wherein said conditions include a GSV of about 4.0 m/s or greater at at least one point in said reaction zone.

87. The method of claim 69 wherein the ratio of the mass of catalyst in said reaction zone to that of the sum of the mass of catalyst in both said reaction zone and said recirculation zone of from about 0.40 to 0.99.

88. The method of claim 69 wherein the ratio of the mass of catalyst in said reaction zone to that of the sum of the mass of catalyst in both said reaction zone and said recirculation zone of from about 0.50 to 0.99.

89. The method of claim 69 wherein the ratio of the mass of catalyst in said reaction zone to that of the sum of the mass of catalyst in both said reaction zone and said recirculation zone of from about 0.30 to about 0.98.

90. The method of claim 69 wherein the ratio of the mass of catalyst in said reaction zone to that of the sum of the mass of catalyst in both said reaction zone and said recirculation zone of from about 0.40 to about 0.98.

91. The method of claim 69 wherein the ratio of the mass of catalyst in said reaction zone to that of the sum of the mass of catalyst in both said reaction zone and said recirculation zone of from about 0.50 to about 0.98.

92. The method of claim 69 wherein the ratio of the mass of catalyst in said reaction zone to that of the sum of the mass of catalyst in both said reaction zone and said recirculation zone of from about 0.30 to about 0.95.

93. The method of claim 69 wherein the ratio of the mass of catalyst in said reaction zone to that of the sum of the mass of catalyst in both said reaction zone and said recirculation zone of from about 0.40 to about 0.95.

94. The method of claim 69 wherein the ratio of the mass of catalyst in said reaction zone to that of the sum of the mass of catalyst in both said reaction zone and said recirculation zone of from about 0.50 to about 0.95.

* * * * *